(12) United States Patent
Ueno et al.

(10) Patent No.: US 11,565,110 B2
(45) Date of Patent: Jan. 31, 2023

(54) SWALLOWING MEDICAL DEVICE, ATTACHMENT UNIT, AND STORAGE MEDIUM

(71) Applicants: J craft Co., Ltd., Osaka (JP); EuSense Medical Co., Ltd., Hyogo (JP); I Medex Co., Ltd., Chiba (JP)

(72) Inventors: Hiroshi Ueno, Osakasayama (JP); Yoshitaka Oku, Nishinomiya (JP)

(73) Assignees: J CRAFT CO., LTD., Izumi (JP); EUSENSE MEDICAL CO., LTD., Nishinomiya (JP); I MEDEX CO., LTD., Chiba (JP)

( * ) Notice: Subject to any disclaimer, the term of this patent is extended or adjusted under 35 U.S.C. 154(b) by 0 days.

(21) Appl. No.: 17/558,612

(22) Filed: Dec. 22, 2021

(65) Prior Publication Data

US 2022/0111204 A1    Apr. 14, 2022

Related U.S. Application Data

(63) Continuation of application No. PCT/JP2020/012352, filed on Mar. 19, 2020.

(30) Foreign Application Priority Data

Jun. 24, 2019    (JP) .............................. JP2019-116091

(51) Int. Cl.
*A61N 1/36*    (2006.01)
*A61B 5/08*    (2006.01)
(Continued)

(52) U.S. Cl.
CPC ........ *A61N 1/36031* (2017.08); *A61B 5/0806* (2013.01); *A61B 5/1135* (2013.01);
(Continued)

(58) Field of Classification Search
CPC ... A61B 2560/04; A61B 5/4848; A61B 5/486; A61B 5/4205; A61B 5/02; A61N 1/05;
(Continued)

(56) References Cited

U.S. PATENT DOCUMENTS 8,388,561 B2    3/2013   Ludlow et al.
9,440,075 B2 *  9/2016   Oku ...................... A61N 1/323
(Continued)

FOREIGN PATENT DOCUMENTS

CN    109414371 A    3/2019
JP    2007-014727 A   1/2007
(Continued)

OTHER PUBLICATIONS

International Search Report and Written Opinion dated May 26, 2020, received for PCT Application PCT/JP2020/012352, Filed on Mar. 19, 2020, 11 pages including English Translation.
(Continued)

*Primary Examiner* — Deborah L Malamud
(74) *Attorney, Agent, or Firm* — Xsensus LLP

(57) ABSTRACT

A swallowing medical device includes: an attachment unit configured to be attached to a target portion of a human body for a medical operation; a control unit configured to control the medical operation; and a storage configured to store use information regarding a use state over time of the attachment unit. The control unit executes a control for restricting use of the attachment unit on the basis of a fact that the use information does not satisfy a set condition for ensuring a characteristic of the attachment unit.

14 Claims, 20 Drawing Sheets

(51) Int. Cl.
*A61B 5/113* (2006.01)
*A61B 5/00* (2006.01)
*A61N 1/04* (2006.01)

(52) U.S. Cl.
CPC .......... *A61B 5/4205* (2013.01); *A61N 1/0452* (2013.01); *A61N 1/36007* (2013.01)

(58) Field of Classification Search
CPC .. A61N 1/0548; A61N 1/0558; A61N 1/3606; A61N 1/36128; A61N 1/36139
See application file for complete search history.

(56) References Cited

U.S. PATENT DOCUMENTS

| | | |
|---|---|---|
| 2015/0165201 A1 | 6/2015 | Oku |
| 2015/0289924 A1 | 10/2015 | Virshek et al. |
| 2017/0188934 A1 | 7/2017 | Rieger et al. |
| 2018/0338789 A1 | 11/2018 | Virshek et al. |
| 2019/0001135 A1 | 1/2019 | Yoo et al. |
| 2019/0125243 A1 | 5/2019 | Oku et al. |
| 2019/0167181 A1 | 6/2019 | Jedwab et al. |
| 2019/0321622 A1 | 10/2019 | Samejima et al. |

FOREIGN PATENT DOCUMENTS

| | | |
|---|---|---|
| JP | 2007-151747 A | 6/2007 |
| JP | 2015-058172 A | 3/2015 |
| JP | 2017-510379 A | 4/2017 |
| JP | 2017-519552 A | 7/2017 |
| JP | 2017-217427 A | 12/2017 |
| JP | 2018-108276 A | 7/2018 |
| WO | 2014/038390 A1 | 3/2014 |
| WO | 2015/183690 A1 | 12/2015 |
| WO | 2018/003127 A1 | 1/2018 |
| WO | 2018/093765 A1 | 5/2018 |
| WO | 2018/119424 A1 | 6/2018 |

OTHER PUBLICATIONS

Office Action dated Jul. 19, 2022, in corresponding Japanese patent Application No. 2021-527373, 13 pages.
Extended European search report dated Jul. 6, 2022, in corresponding European patent Application No. 20831155.5, 9 pages.
Office Action dated Apr. 19, 2022 in Chinese Patent Application No. 202080046127.0, 17 pages.
Office Action dated Apr. 26, 2022 in Japanese Patent Application No. 2021-527373, 16 pages.

* cited by examiner

EMBODIMENT 1

*FIG.4A*

<USE INFORMATION>

| NUMBER OF TIMES | START DAY AND TIME | END DAY AND TIME | USE TIME PERIOD | CUMULATIVE USE TIME PERIOD |
|---|---|---|---|---|
| 1 | 2019.05.08 11:05 | 2019.05.08 11:35 | 0:30 | 0:30 |
| 2 | 2019.05.09 10:25 | 2019.05.09 11:00 | 0:35 | 1:05 |
| 3 | 2019.05.09 15:40 | 2019.05.09 16:12 | 0:32 | 1:37 |
| ⋮ | ⋮ | ⋮ | ⋮ | ⋮ |

*FIG.4B*

<CONFIRMATION INFORMATION>

| SERIAL NUMBER | ENCRYPTION KEY |
|---|---|
| ********* | AAAAAAA |

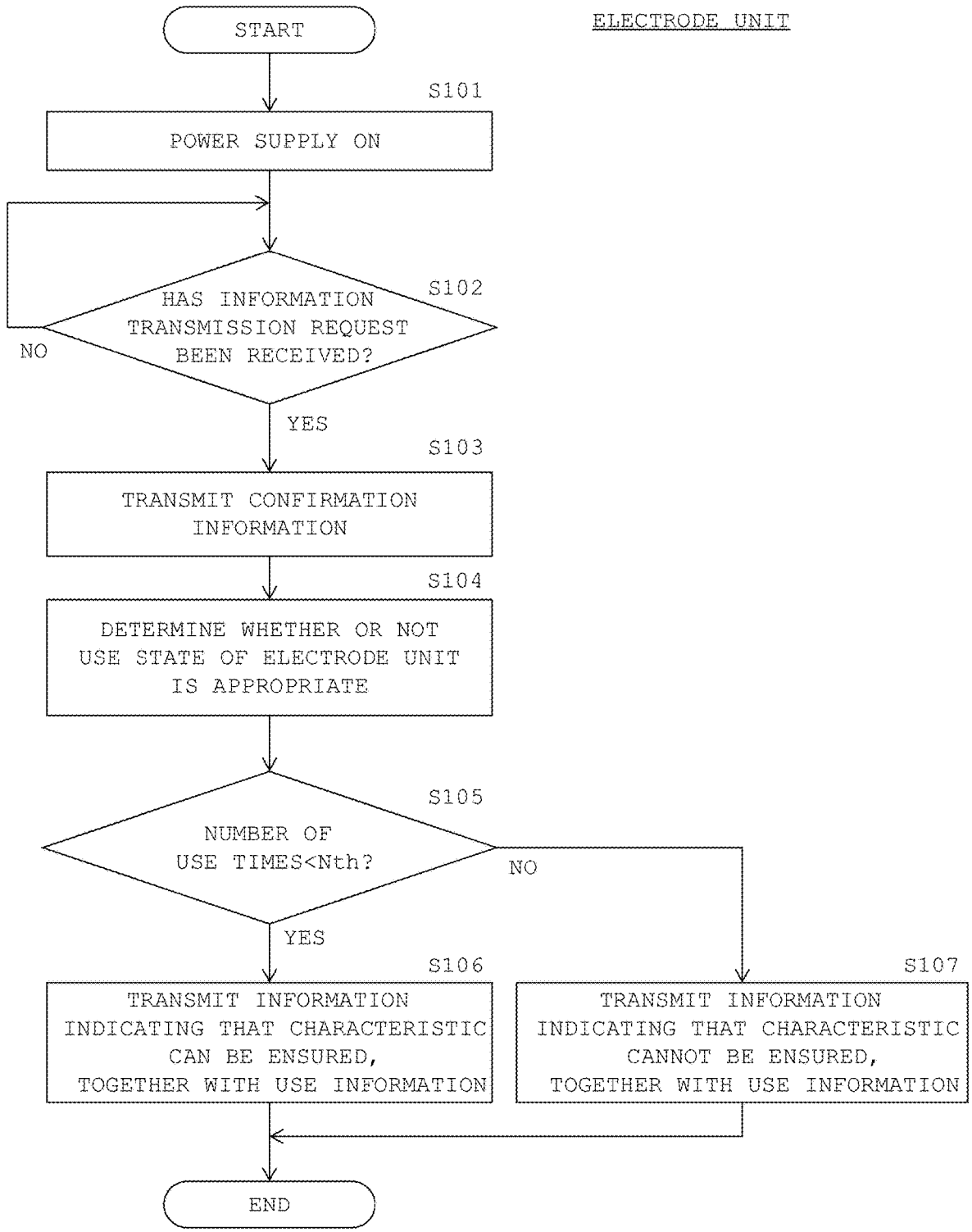

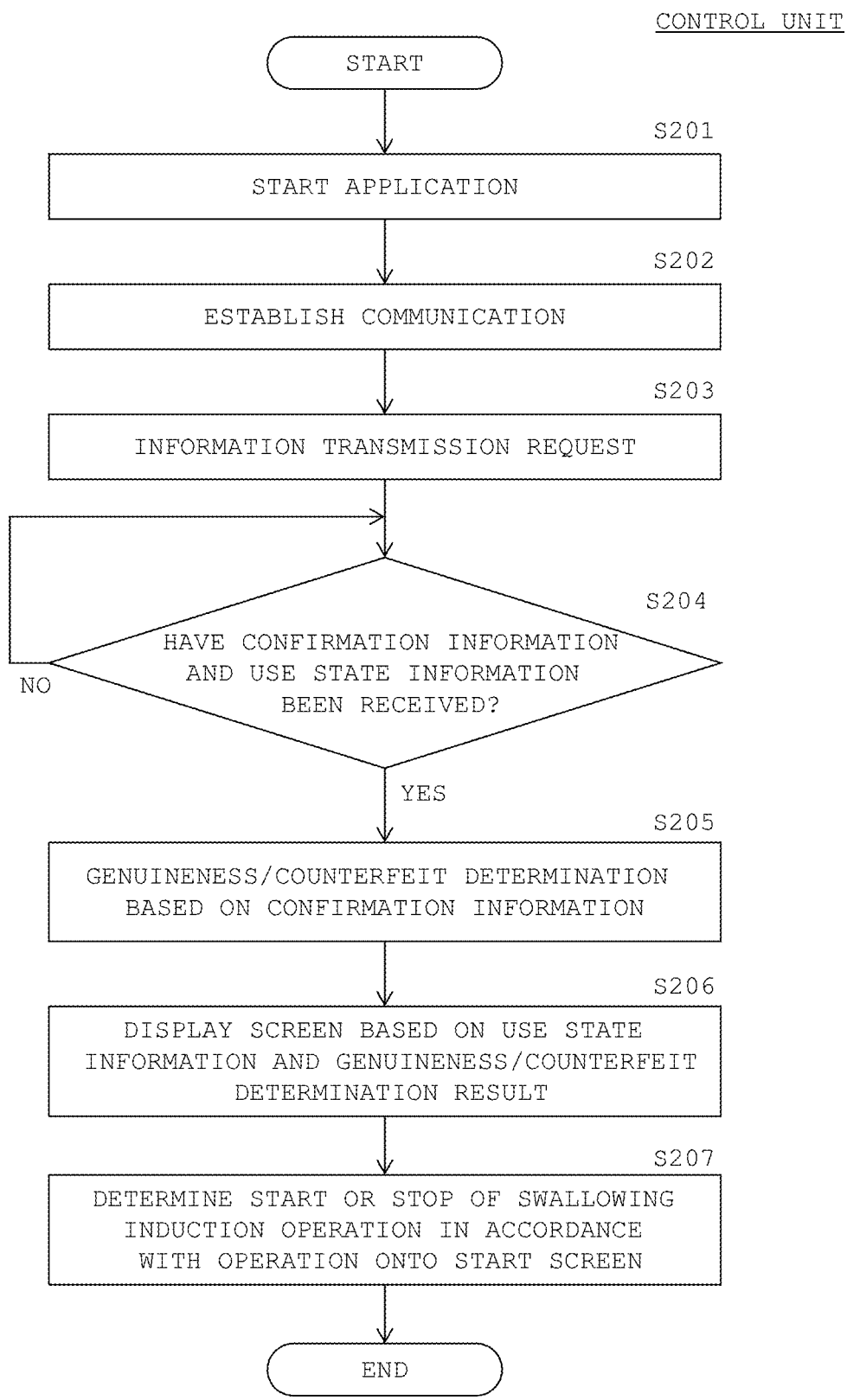

EMBODIMENT 2

FIG.13
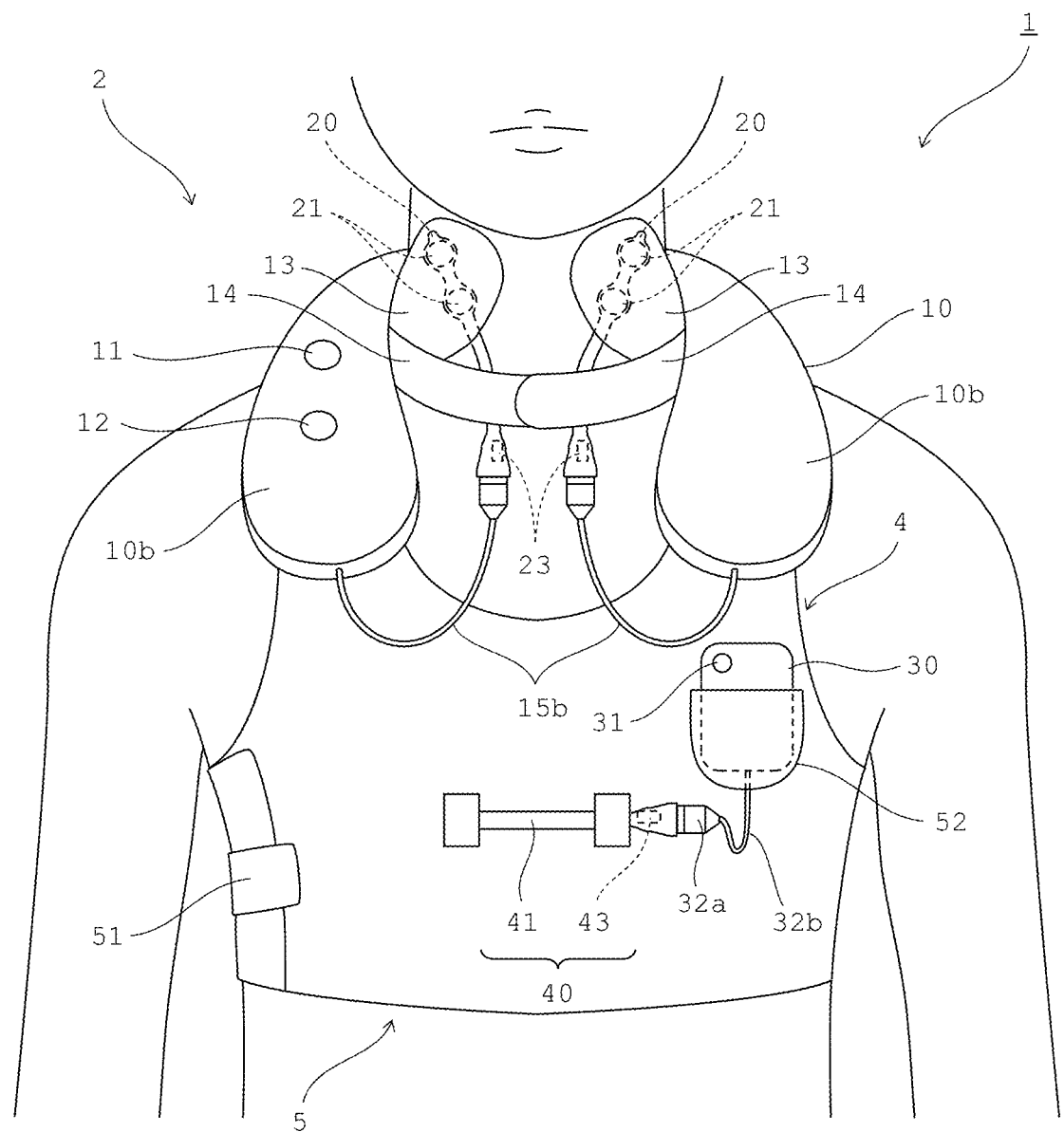
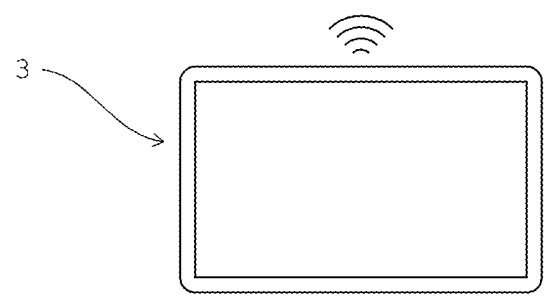

EMBODIMENT 3

_FIG.16_
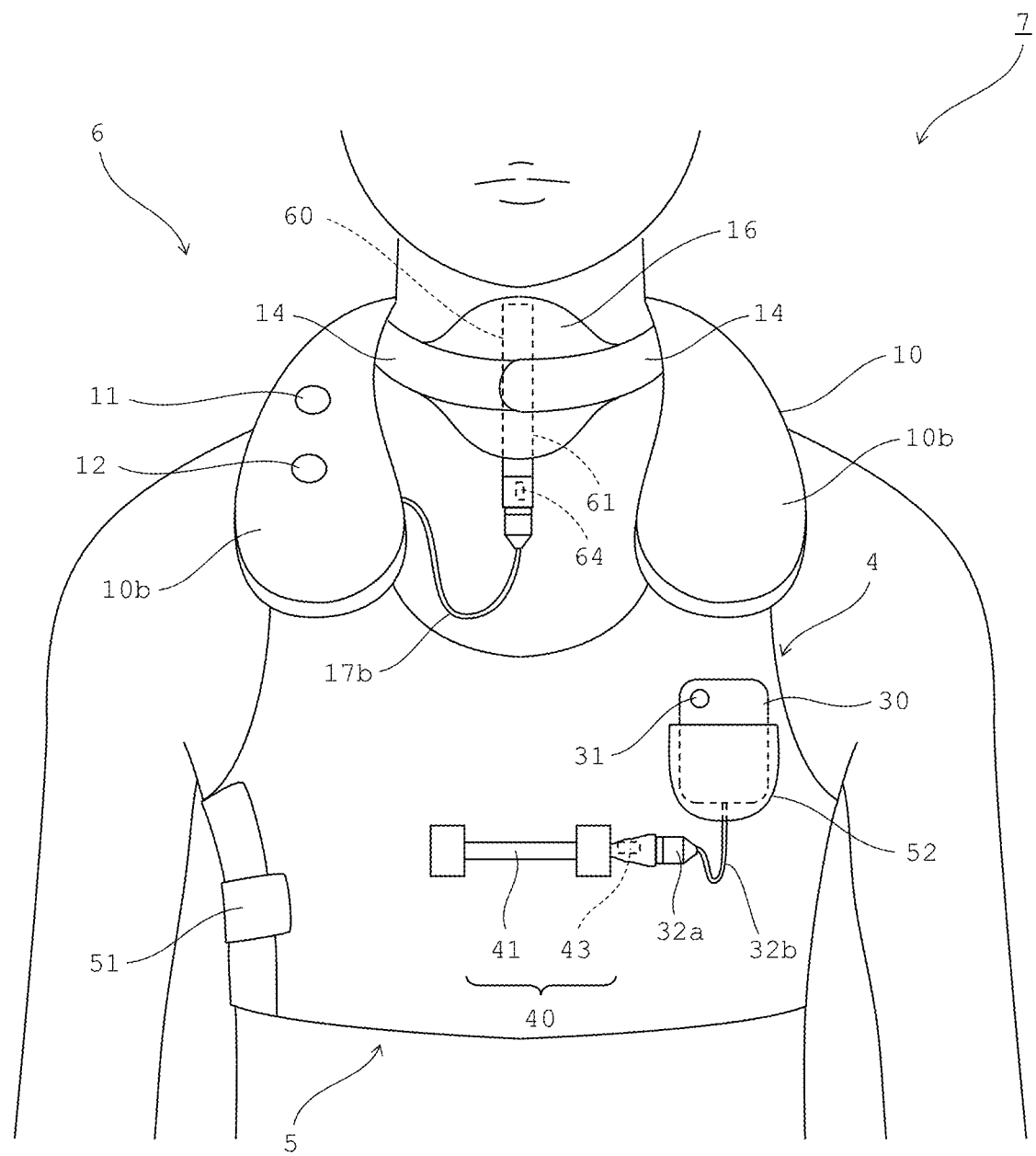

SWALLOWING MEDICAL DEVICE, ATTACHMENT UNIT, AND STORAGE MEDIUM

CROSS-REFERENCE TO RELATED APPLICATIONS

This application is a continuation of International Application No. PCT/JP2020/012352 filed on Mar. 19, 2020, entitled "SWALLOWING MEDICAL DEVICE, ATTACHMENT UNIT, AND PROGRAM", which claims priority under 35 U.S.C. Section 119 of Japanese Patent Application No. 2019-116091 filed on Jun. 24, 2019, entitled "SWALLOWING MEDICAL DEVICE, ATTACHMENT UNIT, AND PROGRAM". The disclosure of the above applications is incorporated herein by reference.

BACKGROUND OF THE INVENTION

1. Field of the Invention

The present invention relates to a swallowing medical device that executes a medical operation regarding swallowing, an attachment unit to be attached to a human body when a medical operation regarding swallowing is performed, and a storage medium having stored therein a program for controlling a medical operation regarding swallowing.

2. Disclosure of Related Art

In recent years, aspiration pneumonia caused by so-called "aspiration" has been a problem, especially, in elderly persons. "Aspiration" is a pathological condition in which swallowing cannot be appropriately performed and the thing having been engulfed enters not the esophagus but the trachea. In order to inhibit aspiration pneumonia, it is effective to cause swallowing at an appropriate timing.

International Publication No. WO2014/038390 describes a device that induces swallowing at an appropriate timing by providing electric stimulation to the pharynx part. In this device, electric stimulation is provided to the nasopharynx nerve of a patient from an electrode adhered to the vicinity of the pharynx part of the patient, whereby swallowing is induced. The electric stimulation is provided in an expiration period of the patient. International Publication No. WO2018/003127 describes a device that monitors swallowing on the basis of detection results of respiration of a patient, swallowing sounds, and displacements of the larynx part and determines a risk of aspiration.

In the configuration described in International Publication No. WO2014/038390, in order to enhance close contact performance with the skin of a patient, an electrically conductive adhesive member, such as a gel sheet, is laid on the upper face of an electrode. Accordingly, the adhesive member comes into close contact with the skin of the patient, and electric stimulation is effectively provided from the electrode to the pharynx part. As a result, swallowing can be appropriately induced from the patient.

However, in this configuration, every time the device is used in treatment or the like of the patient, the adhesive member is attached to the pharynx part in a state of being in close contact with the skin. Therefore, in accordance with the number of use times of the device, sebum and the like of the patient attach to the adhesive member, and as a result, the adhesion force of the adhesive member gradually decreases. In addition, in a case where the adhesive member is an electrically conductive hydrous adhesive gel, sweat and the like due to sweating of the patient permeate the gel, thereby causing decreased adhesive force. Further, due to repeated use, the adhesive force significantly decreases and the close contact performance with the skin is impaired, and thus, the electrical conductivity may be impaired. Similarly, in a case where the adhesive member is an electrically conductive hydrophobic adhesive gel as well, the adhesive force significantly decreases and the close contact performance with the skin is impaired, and thus, the electrical conductivity may be impaired. Thus, when the original characteristics of the adhesive member are not ensured, electric stimulation cannot be appropriately provided to the pharynx part of the patient, and as a result, induction of swallowing may not be appropriately performed.

Similarly, in the configuration of International Publication No. WO2018/003127, it can be assumed that sensors for detecting respiration of a patient and displacements of the larynx part are degraded in association with use. In such a case as well, when degradation of these sensors has occurred, respiration of the patient and displacements of the larynx part cannot be appropriately detected, and as a result, monitoring of swallowing may not be appropriately performed.

SUMMARY OF THE INVENTION

A first mode of the present invention relates to a swallowing medical device configured to execute a medical operation regarding swallowing. The swallowing medical device according to the present mode includes: an attachment unit configured to be attached to a target portion of a human body for the medical operation; a control unit configured to control the medical operation; and a storage configured to store use information regarding a use state over time of the attachment unit. The control unit executes a control for restricting use of the attachment unit on the basis of a fact that the use information does not satisfy a set condition for ensuring a characteristic of the attachment unit.

According to the swallowing medical device of the present mode, when the use information regarding the use state of the attachment unit does not satisfy the set condition for ensuring the characteristic of the attachment unit, a control for restricting use of the attachment unit is performed. Therefore, appropriateness of the medical operation regarding swallowing can be ensured.

A second mode of the present invention relates to an attachment unit being replaceable and being configured to be attached to a target portion for a medical operation regarding swallowing. The attachment unit according to this mode includes: a storage configured to store use information regarding a use state over time of the attachment unit; and a controller configured to transmit information based on the use information, to a control unit configured to execute the medical operation by using the attachment unit.

According to the attachment unit of the present mode, when the use information does not satisfy the set condition for ensuring the characteristic of the attachment unit, a control for restricting use of the attachment unit can be performed in the control unit. Therefore, appropriateness of the medical operation regarding swallowing can be ensured.

A third mode of the present invention is a storage medium having stored therein a program configured to cause a controller of a control unit to execute a predetermined function. The controller executes a medical operation regarding swallowing by using an attachment unit configured to be attached to a target portion of a human body. The program causes the controller to execute a function of restricting use of the attachment unit on the basis of a fact that use information regarding a use state over time of the attachment unit does not satisfy a set condition for ensuring a characteristic of the attachment unit.

The above and other objects and new features of the present invention will be fully clarified by the following description of the embodiment, when read in conjunction with accompanying drawings.

BRIEF DESCRIPTION OF THE DRAWINGS

FIG. 4A shows a configuration of use information according to Embodiment 1. FIG. 4B shows a configuration of confirmation information according to Embodiment 1;

FIG. 6 is a flow chart showing a control executed by a controller of an electrode unit when a swallowing induction operation is started, according to Embodiment 1;

FIG. 7 is a flow chart showing a control executed by a controller of the control unit when a swallowing induction operation is started, according to Embodiment 1;

FIG. 13 shows a state where the electric stimulation device and the respiration detection device have been attached to a patient, according to Embodiment 2;

FIG. 16 shows a state where the respiration detection device and the swallowing monitoring device have been attached to a patient, according to Embodiment 3;

It should be noted that the drawings are solely for description and do not limit the scope of the present invention by any degree.

DESCRIPTION OF PREFERRED EMBODIMENTS

Hereinafter, embodiments of the present invention will be described with reference to the drawings.

Embodiment 1

Embodiment 1 has been made by applying the present invention to a swallowing induction device 1 for inducing swallowing in a patient in order to treat aspiration, for example.

In Embodiment 1, the swallowing induction device 1 and an electric stimulation device 2 correspond to a "swallowing medical device" described in the claims, and an electrode unit 20 corresponds to an "attachment unit" described in the claims. However, Embodiment 1 described below is merely a configuration example obtained through implementation of the present invention, and does not limit the invention according to the claims in any way.

Figure 1:
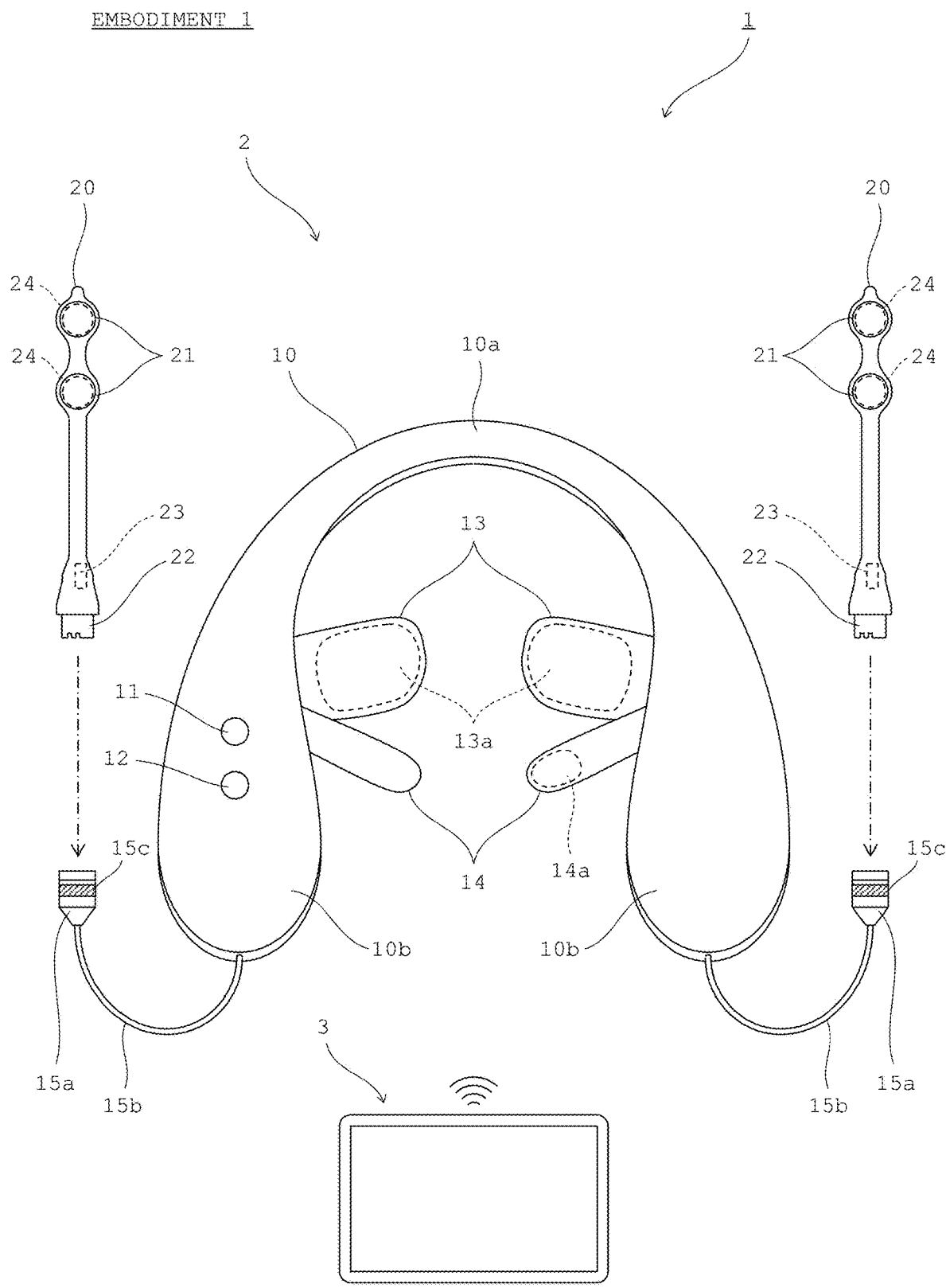
FIG. 1 shows a configuration of a swallowing induction device according to Embodiment 1.
Figure 2:
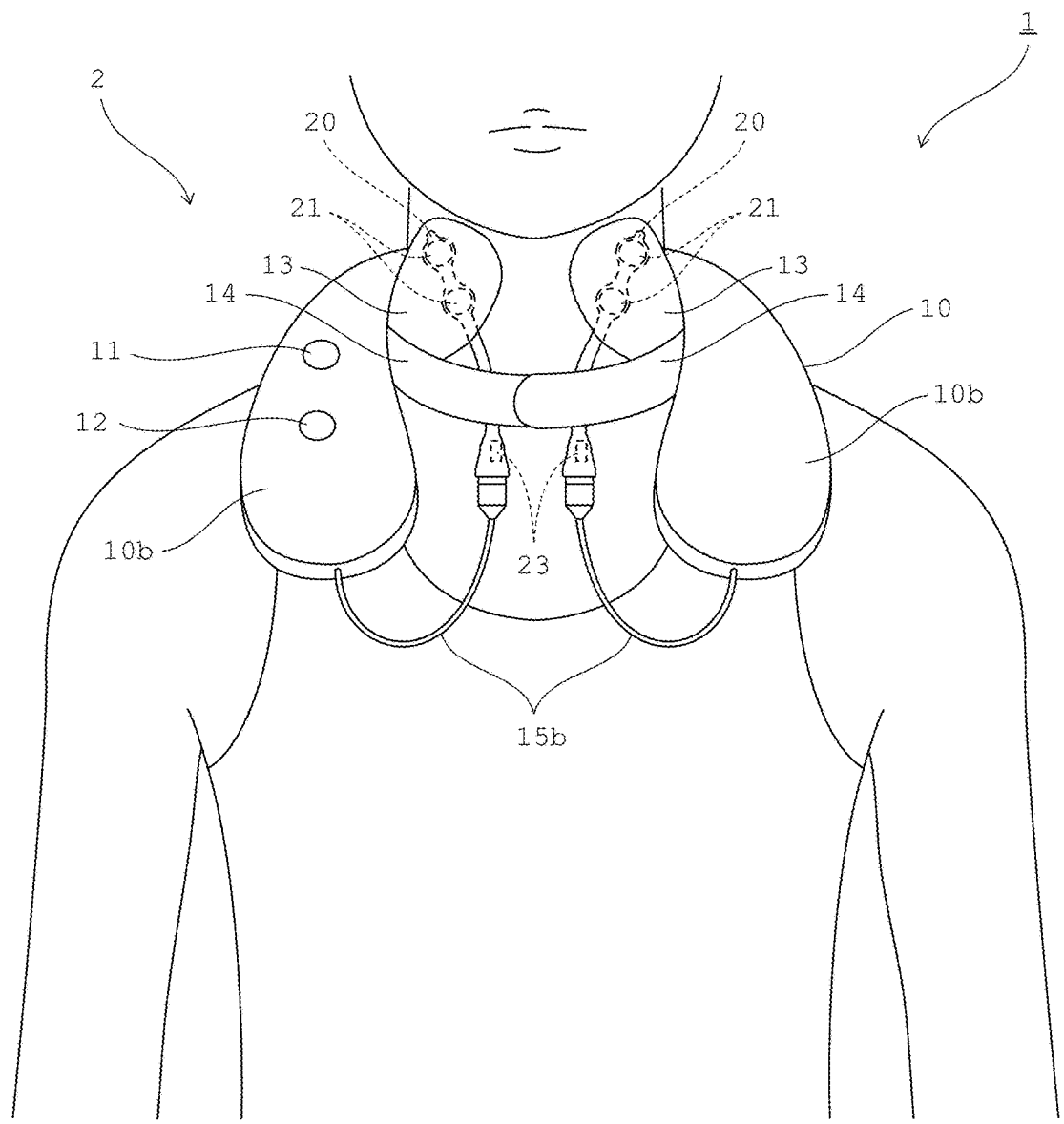
FIG. 2 shows a use state of the swallowing induction device according to Embodiment 1.

FIG. 1 shows a configuration of the swallowing induction device 1 according to Embodiment 1. FIG. 2 shows a use state of the swallowing induction device 1.

As shown in FIG. 1, the swallowing induction device 1 includes the electric stimulation device 2 and a control unit 3. The electric stimulation device 2 provides electric stimulation to the pharynx part of a patient. The control unit 3 performs a control for inducing swallowing, on the electric stimulation device 2. The electric stimulation device 2 and the control unit 3 are communicable with each other through wireless communication according to Bluetooth (registered trademark) or the like. For example, the control unit 3 is implemented by a tablet. The control unit 3 may be another information terminal device such as a mobile phone. The electric stimulation device 2 and the control unit 3 may be communicable with each other through wired communication. The control unit 3 may be individually communicable with a plurality of electric stimulation devices 2 that are different from each other.

The electric stimulation device 2 includes a holder unit 10 and electrode units 20. The holder unit 10 has a shape that fits the neck of the patient. That is, the holder unit 10 has a shape in which two end parts 10b that, when attached, dangle to the vicinity of the upper part of the chest of the patient are connected by a connection part 10a. When the holder unit 10 is attached, the connection part 10a curves around the back of the neck of the patient. The outer-side face of the holder unit 10 is formed from an ABS material, for example. Preferably, the connection part 10a wound around the neck is formed from a soft material such as an EVA material, for example. The obverse surfaces or the like of the two end parts 10b may be provided with symbols (left/right, L/R) or the like for indicating which side of left and right of the neck of the patient each end part 10b is to be put on.

In the holder unit 10, a power supply button 11 and an emergency stop button 12 are disposed on the obverse surface of one end part 10b. The power supply button 11 is a button for operating the electric stimulation device 2. The emergency stop button 12 is a button for executing emergency stop of operation of the electric stimulation device 2. A circuit board is enclosed in the depth direction with respect to the power supply button 11 and the emergency stop button 12. This circuit board has mounted thereon a communication part for performing wireless communication with the control unit 3, a controller for driving each electrode unit 20 on the basis of a control signal from the control unit 3, and the like.

Elastic press members 13 are attached to inner-side faces of the two end parts 10b, respectively. Each press member 13 is for pressing an electrode portion of a corresponding electrode unit 20 to the neck of the patient when the holder unit 10 has been attached to the patient. The press member 13 is formed in a bag shape by using a stretchable cloth, for example, and a cushioning member 13a such as microbeads is enclosed inside this bag.

Belts 14 in strip shapes are further attached to the inner-side faces of the two end parts 10b. Each belt 14 is for fixing the holder unit 10 to the neck of the patient. A fastening part 14a serving as one side of a Hook-and-Loop fastener is provided on the inner-side face of one belt 14. The entirety of the outer-side face of the other belt 14 serves as the other fastening part of the Hook-and-Loop fastener. When the fastening part 14a of one belt 14 is laid on the outer-side face of the other belt 14, the two belts 14 are joined to each other. When the two belts 14 being overlaid with each other are detached, joining of the two belts 14 is released.

Cables 15b are drawn from the lower ends of the two end parts 10b, respectively. Each cable 15b is connected to the above-described circuit board built in the holder unit 10. A connector 15a for connecting a corresponding electrode unit 20 is attached to the leading end of the cable 15b. As indicated by the arrows of alternate long and short dash lines in FIG. 1, a terminal 22 of the electrode unit 20 is inserted into the connector 15a.

Each connector 15a is provided with a structure for fixing the inserted terminal 22. For example, a lever 15c for switching between fixation and release is provided to the outer-side face of the connector 15a. When the lever 15c is lifted from the outer-side face of the connector 15a, attachment/detachment of the terminal 22 with respect to the connector 15a is enabled. In this state, when the terminal 22 is inserted into the connector 15a, and then the lever 15c is pushed down to the outer-side face of connector 15a, the terminal 22 is fixed to the connector 15a.

Each electrode unit 20 has a thin-plate-like structure having flexibility. In a plan view, the electrode unit 20 has a shape that is slender in one direction. Two adhesive members 21 are disposed on the inner-side face of one end part of the electrode unit 20, and electrodes 24 are disposed on the inner side of these adhesive members 21. Each adhesive member 21 is electrically conductive. The adhesive member 21 is implemented by a pad formed from a gel material, for example. As the gel material, an electrically conductive hydrous adhesive gel or an electrically conductive hydrophobic adhesive gel can be used.

The terminal 22 protrudes from the other end part of the electrode unit 20. A circuit board is built in the other end part of the electrode unit 20, and the terminal 22 is connected to this circuit board. A storage 23 implemented by an EEPROM, for example, is mounted to this circuit board. As described later, the storage 23 stores use information regarding the use state over time of the electrode unit 20, confirmation information for confirming that the electrode unit 20 is a genuine article, and the like.

When the electric stimulation device 2 is not in a use state, the electrode unit 20 is removed from the connector 15a and stored by use of a storage sheet (model sheet) so as not to be exposed to moisture or sunlight. When the electric stimulation device 2 is used, the electrode unit 20 is attached to the connector 15a to be integrated with the holder unit 10.

Then, the connection part 10a of the holder unit 10 is hung around the neck of the patient, and end parts of the two electrode units 20 are put onto portions on the left side and the right side of the larynx part of the patient. At this time, the adhesive members 21 disposed in the end part of each electrode unit 20 adhere to the surface of the skin. In this state, the two press members 13 are respectively put on the upper faces of the end parts of the electrode units 20, and further, the two belts 14 are overlaid with each other to be joined. At this time, the press members 13 are deflected, and due to the reaction force thereof, the end parts of the electrode units 20 are pressed against the neck of the patient. In this manner, as shown in FIG. 2, the electrode units 20 are attached to the patient in a state where the adhesive members 21 are pressed against the neck of the patient.

Then, when the electrode units 20 are driven by the control unit 3, current flows in the electrodes 24 disposed on the inner side of the adhesive members 21, whereby a swallowing reflex is promoted. Two electrodes 24 are set to be a positive electrode and a negative electrode, and the remaining two electrodes 24 are set to be a positive electrode and a negative electrode. The four electrodes 24 are disposed such that a pair of a positive electrode and a negative electrode and another pair of a positive electrode and a negative electrode are arranged in an X-shape with the thyroid cartilage set as the center. The two pairs of electrodes 24 are driven such that: two pairs of electrodes 24 each have a medium frequency; and the difference in the frequencies of the two pairs of electrodes 24 is a low frequency. Accordingly, an interference wave of a low frequency according to the difference between these frequencies is generated in a deep portion, and the superior laryngeal nerve is stimulated by this interference wave. Accordingly, an afferent signal transmitted from the pharynx/larynx to the brain stem via the superior laryngeal nerve is enhanced, and a swallowing reflex is promoted. When an interference wave caused by the two pairs of electrodes is used, swallowing can be effectively promoted while discomfort and pain in the skin are suppressed.

Figure 3:
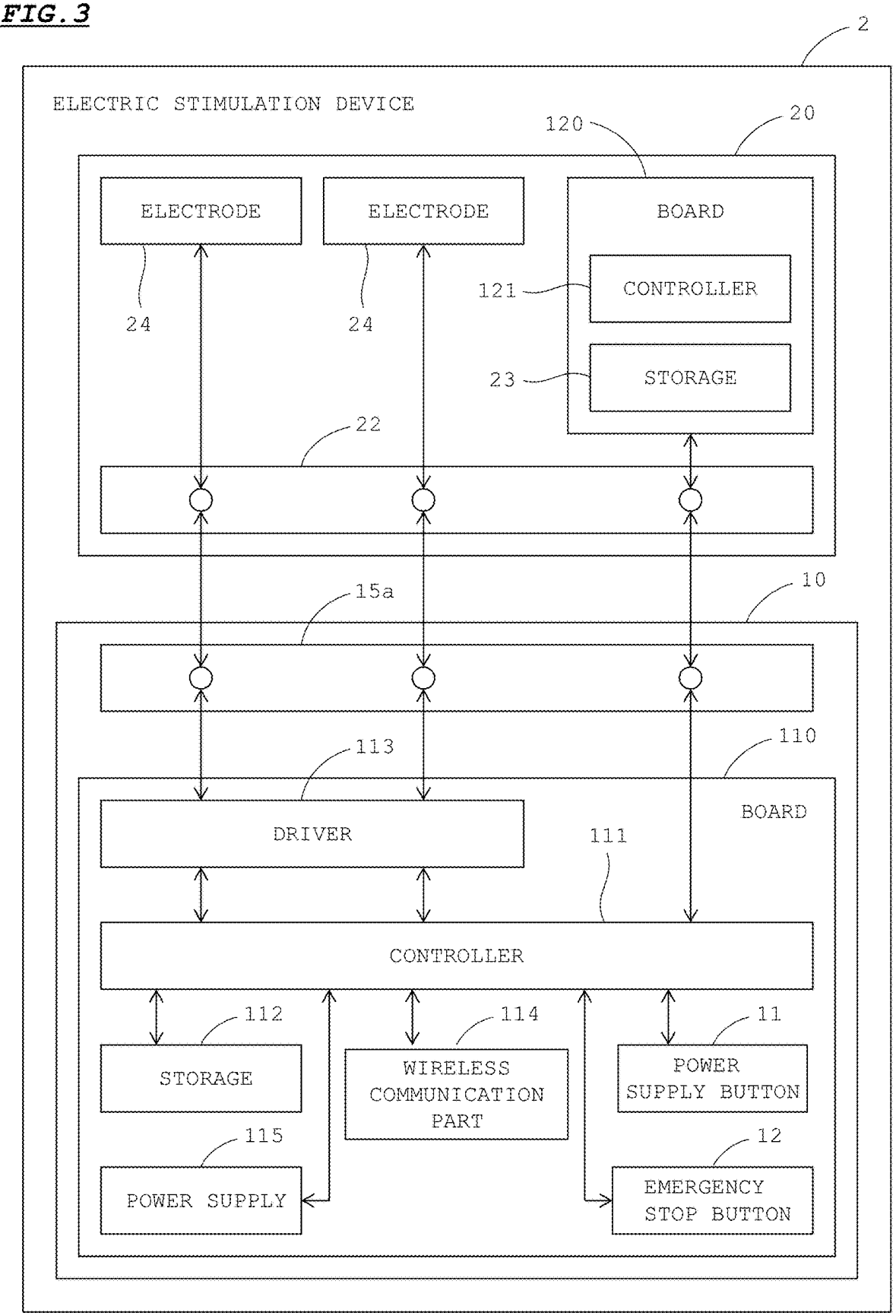
FIG. 3 is a block diagram showing a circuit configuration of an electric stimulation device according to Embodiment 1.

FIG. 3 is a block diagram showing a circuit configuration of the electric stimulation device 2.

For convenience, FIG. 3 shows one of the two electrode units 20 attached to the holder unit 10. However, the other electrode unit 20 also has the same configuration. A combination of a driver 113, a connector 15a, and the other electrode unit 20 is further added to the configuration shown in FIG. 3.

The holder unit 10 and the electrode unit 20 include circuit boards 110, 120, respectively. As described above, the circuit board 110 is built in the holder unit 10. The circuit board 120 is built in the end part on the terminal 22 side of the electrode unit 20. These circuit boards 110, 120 are connected to each other by the terminal 22 being connected to the connector 15a.

The circuit board 110 of the holder unit 10 has mounted thereon a controller 111, a storage 112, a driver 113, a wireless communication part 114, and a power supply 115. Other than these, the power supply button 11 and the emergency stop button 12 shown in FIG. 1 are also provided on the circuit board 110.

The controller 111 is implemented by a microcomputer, for example, and controls components in accordance with a program stored in the storage 112. The storage 112 is implemented by a ROM, a RAM, etc., and stores a program for controlling components. The storage 112 is used as a work area when the controller 111 controls components.

The driver 113 drives the electrodes 24 in accordance with control from the controller 111. The wireless communication part 114 performs wireless communication with the control unit 3 in accordance with control from the controller 111. The power supply 115 includes a battery and supplies a power supply voltage to circuit parts of the circuit boards 110, 120. The power supply voltage is supplied to the circuit board 120 on the electrode unit 20 side via the cable 15b shown in FIG. 1.

The circuit board 120 of the electrode unit 20 has mounted thereon a controller 121 and the storage 23. The controller 121 is implemented by a microcomputer, for example, and controls components in accordance with a program stored in the storage 23. The controller 121 has a clock function of clocking the present day and time. The storage 23 is implemented by a ROM, a RAM, etc., and stores a program for controlling components. The storage 23 is used as a work area when the controller 121 controls components.

The storage 23 includes a nonvolatile memory (EEPROM) for which data is writable and erasable. The storage 23 stores, into this nonvolatile memory, use information regarding the use state of the electrode unit 20. In addition, the storage 23 stores, into a predetermined area other than the writing area of the use information in this nonvolatile memory, confirmation information for confirming that the electrode unit 20 is a genuine article, i.e., that the electrode unit 20 has been manufactured by an appropriate manufacturer.

FIG. 4A shows a configuration of the use information, and FIG. 4B shows a configuration of the confirmation information.

As shown in FIG. 4A, the use information is composed of: the number of times the electrode unit 20 has been used; the start day and time, the end day and time, and the use time period of each use; and the cumulative use time period from the time point of the first use of the electrode unit 20. The use time period is calculated as a difference between the start day and time and the end day and time. Each cumulative use time period is calculated by adding the use time periods up to the corresponding number of use times.

The use information may be composed only of the start day and time and the end day and time. In this case, the number of sets of the start day and time and the end day and time stored in the storage 23 is the number of use times. The use time period and the cumulative use time period can be calculated as needed through the above calculation on the basis of the start day and time and the end day and time stored in the storage 23.

Alternatively, the use information may be composed only of the use time period. In this case, the number of use time periods stored in the storage 23 is the number of use times. The cumulative use time period can be calculated as needed by adding the use time periods.

As shown in FIG. 4B, the confirmation information is composed of a serial number having a predetermined number of digits, and an encryption key. The serial number is encrypted by the encryption key, and when data in a memory area in which the serial number is stored is decrypted by the encryption key, the serial number having a predetermined number of digits is obtained.

Figure 5:
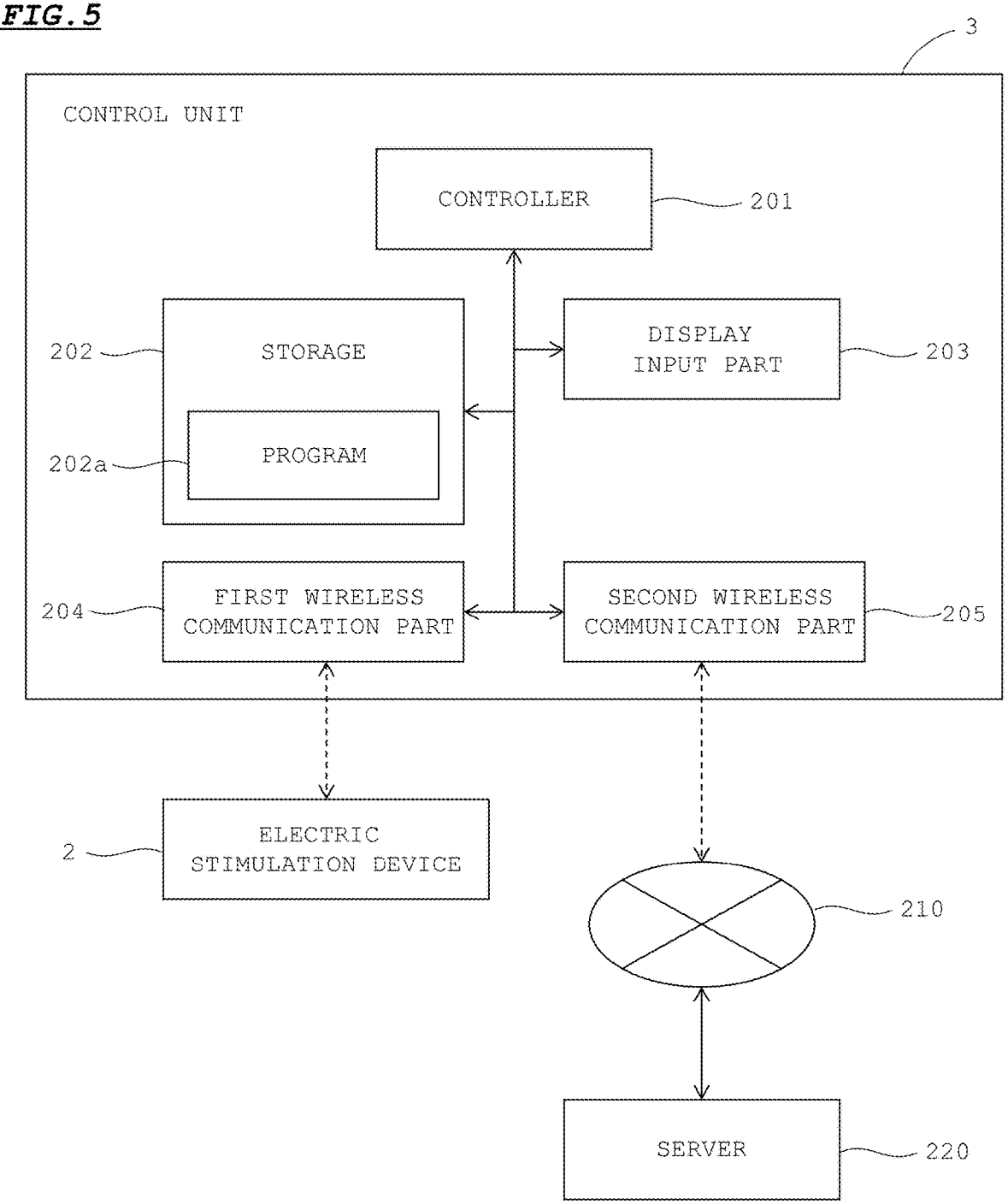
FIG. 5 shows a circuit configuration of a control unit according to Embodiment 1.

FIG. 5 shows a circuit configuration of the control unit 3.

The control unit 3 includes a controller 201, a storage 202, a display input part 203, a first wireless communication part 204, and a second wireless communication part 205.

The controller 201 is implemented by an arithmetic processing circuit such as a CPU, for example, and controls components in accordance with a program 202a stored in the storage 202. The storage 202 is implemented by a ROM, a RAM, etc., and stores the program 202a for controlling a swallowing induction operation. The storage 202 is used as a work area when the controller 201 controls components.

The display input part 203 displays predetermined information and receives an operation input from a user. The display input part 203 is implemented by a touch panel, for example. In a case where the control unit 3 is a tablet, substantially the entirety of the front face of the control unit 3 serves as the region where the display input part 203 is disposed.

The first wireless communication part 204 performs wireless communication with the wireless communication part 114 of the electric stimulation device 2 in accordance with control from the controller 201. The second wireless communication part 205 communicates with a server 220 connected to an external communication network 210, in accordance with control from the controller 201. The external communication network 210 is a public line, for example. The server 220 manages various types of information regarding the swallowing induction operation.

The program 202a for controlling the swallowing induction operation is downloaded from the server 220 to the control unit 3 via the second wireless communication part 205, and installed into the storage 202. Other than this, the program 202a may be taken into the control unit 3 via a USB memory or an optical disk, and installed into the storage 202.

FIG. 6 is a flow chart showing a control executed by the controller 121 of the electrode unit 20 when a swallowing induction operation is started. FIG. 7 is a flow chart showing a control executed by the controller 201 of the control unit 3 when a swallowing induction operation is started.

A user such as a doctor attaches each electrode unit 20 to a patient as shown in FIG. 2, then, starts an application based on the program 202a installed in the control unit 3, and further, operates the power supply button 11 of the holder unit 10 to turn on the power supply to the electric stimulation device 2.

As shown in FIG. 6, when the power supply has been turned on (S101), the controller 121 of the electrode unit 20 waits for an information transmission request to be transmitted from the control unit 3 (S102). As shown in FIG. 7, when an application based on the program 202a has been started (S201), the controller 201 of the control unit 3 establishes communication with the electric stimulation device 2 via the first wireless communication part 204 (S202). Upon establishment of the communication, the controller 201 transmits, to the electric stimulation device 2, a transmission request for confirmation information and use information (S203), and waits for the confirmation information and the use information to be transmitted from the electric stimulation device 2 (S204). The transmitted transmission request is transferred to the controller 121 of the electrode unit 20 via the controller 111 disposed on the circuit board 110 of the electric stimulation device 2.

With reference to FIG. 6, when the controller 121 of the electrode unit 20 has received the information transmission request from the control unit 3 (S102: YES), the controller 121 reads out data from the storage area of confirmation information on the storage 23, and transmits the read out data to the control unit 3 via the controller 111 disposed on the circuit board 110 (S103). Further, the controller 121 reads out data from the storage area of use information on the storage 23, and determines, on the basis of the read out data, whether or not the use state of the electrode unit 20 is appropriate (S104).

Specifically, the controller 121 obtains the number of use times of the electrode unit 20 from the use information, and determines whether or not the number of use times satisfies a set condition for ensuring the characteristics of the electrode unit 20, i.e., whether or not the number of use times is less than an upper limit number of times Nth that can ensure the characteristics of the electrode unit 20 (S105). Here, the upper limit number of times Nth is set on the basis of degradation over time of the adhesive members 21 provided to the electrode unit 20.

That is, every time the electric stimulation device 2 is used in treatment or the like of the patient, each adhesive member 21 comes into close contact with the skin of the patient. Therefore, sebum and the like of the patient attach to the adhesive member 21 in accordance with the number of use times of the electrode unit 20, and as a result, the adhesion force of the adhesive member 21 gradually decreases. In a case where the adhesive member 21 has a water absorbing property, sweat and the like of the patient permeate the adhesive member 21, and the original characteristics of the adhesive member 21 may not be ensured. Alternatively, in a case where the adhesive member 21 has a non-water-absorbing property, moisture in the adhesive member 21 evaporates, whereby the adhesion force of the adhesive member 21 may decrease. Thus, in a case where the original characteristics of the adhesive member 21 are not ensured, electric stimulation cannot be appropriately provided to the pharynx part of the patient, and as a result, induction of swallowing may not be appropriately performed.

From this viewpoint, the upper limit number of times Nth is set to a number of use times at which the adhesiveness is assumed to remain in the adhesive member 21 to an extent that induction of swallowing can be appropriately performed. For example, the upper limit number of times Nth is set to about 14 times to 20 times. The upper limit number of times Nth is set in advance in the program 202a. The upper limit number of times Nth may be adjustable from the default value by the user.

When the number of use times of the electrode unit 20 is less than the upper limit number of times Nth (S105: YES), the controller 121 transmits, to the control unit 3, use state information that includes: information indicating that the characteristics of the electrode unit 20 can be ensured; and the use information read out from the storage 23 (S106). On the other hand, when the number of use times of the electrode unit 20 is not less than the upper limit number of times Nth (S105: NO), the controller 121 transmits, to the control unit 3, use state information that includes: information indicating that the characteristics of the electrode unit 20 cannot be ensured; and the use information read out from the storage 23 (S107). These pieces of information are also transmitted to the control unit 3 via the controller 111 disposed on the circuit board 110.

The processes of steps S101 to S107 are performed for each of the two electrode units 20 connected to the holder unit 10. Therefore, for each of these two electrode units 20, the confirmation information and the use state information are transmitted to the control unit 3.

With reference to FIG. 7, when the controller 201 of the control unit 3 has received the confirmation information and the use state information from the electrode unit 20 (S204: YES), the controller 201 first determines whether the electrode unit 20 is genuine or counterfeit, on the basis of the received confirmation information (S205). Specifically, the controller 201 decrypts the serial number on the basis of the encryption key included in the confirmation information. Then, the controller 201 determines whether the electrode unit 20 is genuine or counterfeit, on the basis of whether or not the number of digits of the decrypted serial number is the number of digits determined in advance.

Further, the controller 201 inquires of the server 220 whether the decrypted serial number is not doubly registered in the server 220, and determines, on the basis of the response thereto, whether the electrode unit 20 is genuine or counterfeit.

For example, the controller 201 transmits, to the server 220, the decrypted serial number together with the code number of the medical facility where the control unit 3 is used. The server 220 registers, into a database, the received serial number in association with the code number of the medical facility. Here, in a case where the confirmation information of the electrode unit 20 being a genuine article is copied as is to a storage 23 of an electrode unit 20 being an imitation article, a plurality of identical serial numbers are registered in the server 220 in association with code numbers of different medical facilities, for example. When the serial number received from the controller 201 is registered in association with code numbers of different medical facilities, the server 220 transmits, to the controller 201, a response indicating that there is a double registration (that the electrode unit 20 is an imitation article). On the other hand, when the serial number received from the controller 201 is not registered in association with code numbers of different medical facilities, the server 220 transmits, to the controller 201, a response indicating that there is no double registration (that the electrode unit 20 is a genuine article).

In this manner, after determining whether the electrode unit 20 is genuine or counterfeit, the controller 201 causes the display input part 203 to display a start screen based on the genuineness/counterfeit determination result and the use state information received in step S204 (S206). In accordance with an operation from the user onto the start screen, the controller 201 starts the swallowing induction operation, or stops the swallowing induction operation (S207). Then, the process at the time of start of swallowing induction ends.

Figure 8A:
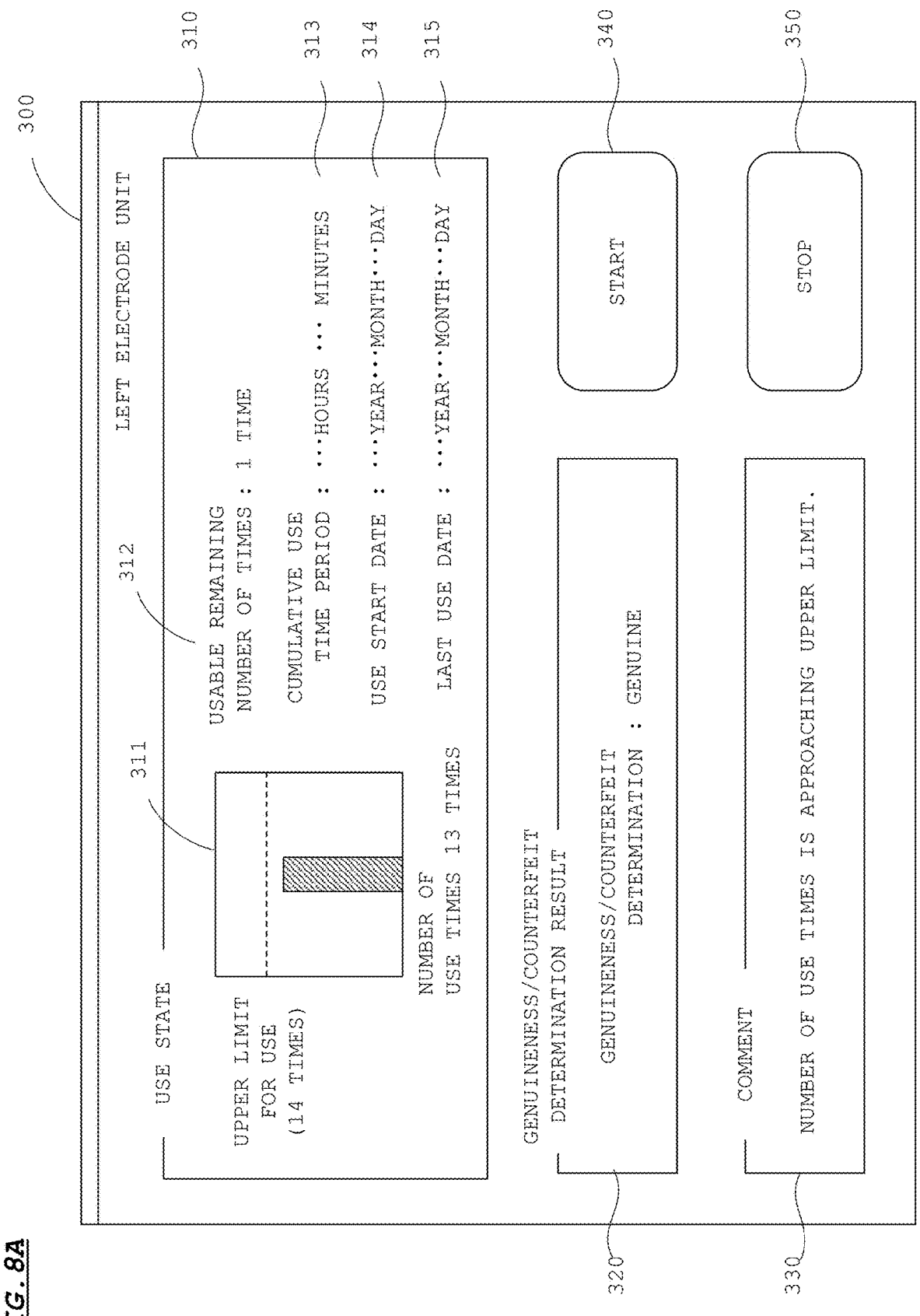
FIGS. 8A, 8B each show a configuration of a start screen displayed at the time of start of a swallowing induction operation according to Embodiment 1.
Figure 8B:
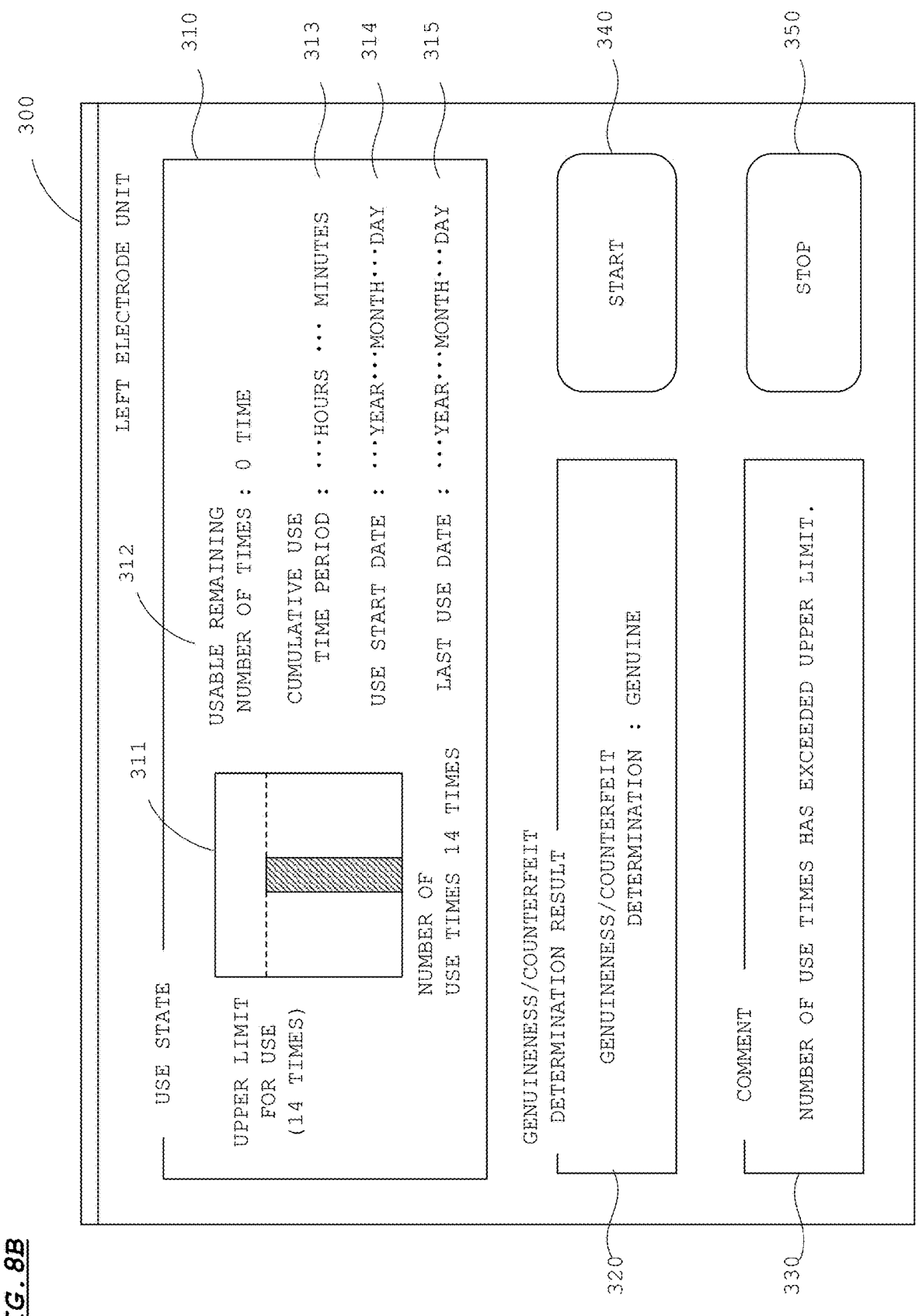
Figure 9A:
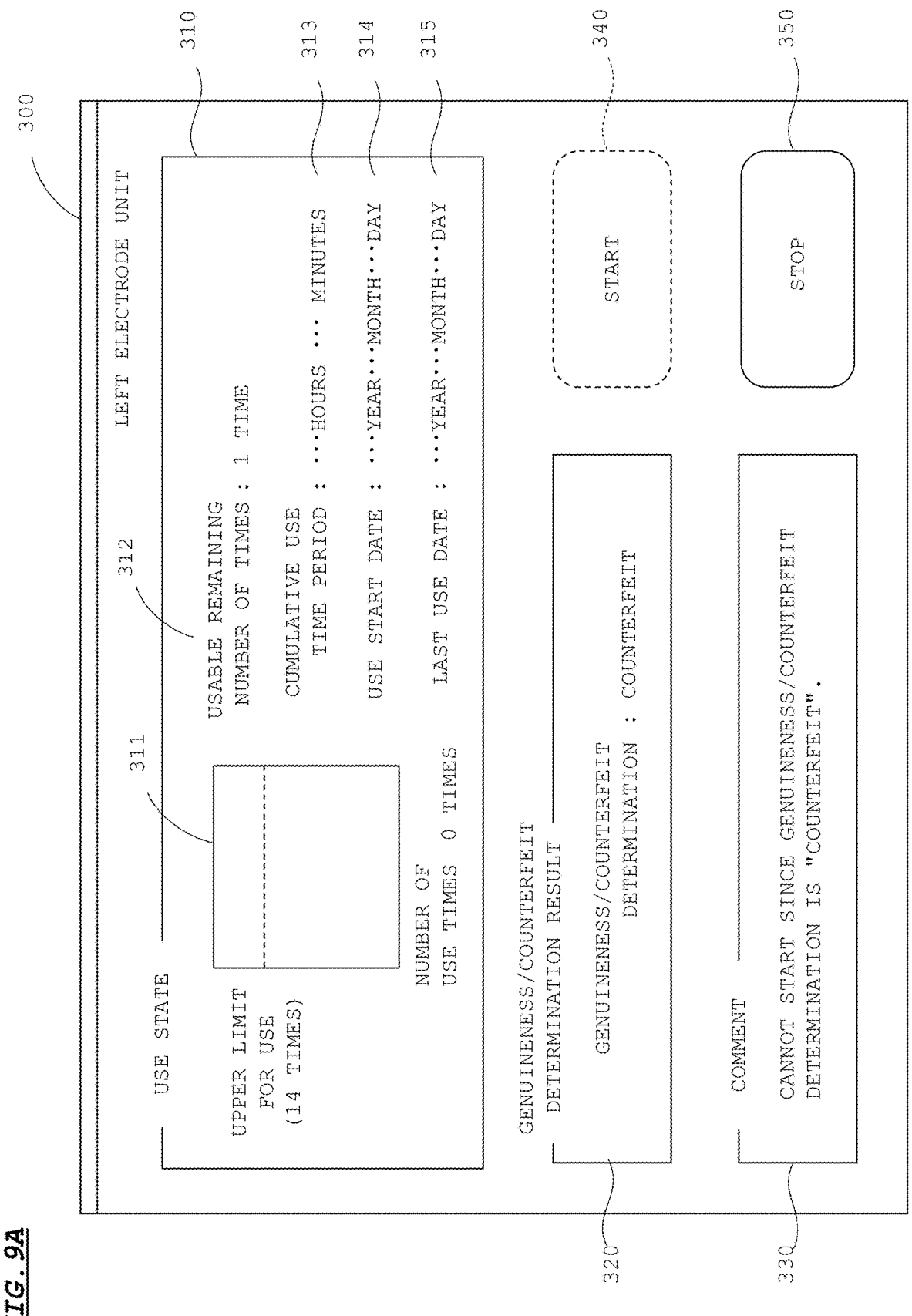
FIG. 9A shows a configuration of a start screen displayed at the time of start of a swallowing induction operation according to Embodiment 1.

FIGS. 8A, 8B and FIG. 9A each show a configuration of a start screen 300 displayed in step S206.

FIG. 8A is a start screen 300 in a case where the genuineness/counterfeit determination result regarding the electrode unit 20 is "genuine" and the number of use times of the electrode unit 20 has not reached the upper limit number of times Nth. FIG. 8B is a start screen 300 in a case where the genuineness/counterfeit determination result regarding the electrode unit 20 is "genuine" and the number of use times of the electrode unit 20 has reached the upper limit number of times Nth. FIG. 9A is a start screen 300 in a case where the genuineness/counterfeit determination result regarding the electrode unit 20 is "counterfeit" and the number of use times of the electrode unit 20 has not reached the upper limit number of times Nth. Here, the upper limit number of times Nth is set to 14 times.

FIGS. 8A, 8B and FIG. 9A each show a start screen 300 regarding one (here, the electrode unit 20 on the left side) of the two electrode units 20 attached to the holder unit 10. In these start screens 300, when a start button 340 has been operated, the start screen 300 regarding the other electrode unit 20 (here, the electrode unit 20 on the right side) is displayed. Instead of this display method, the start screen 300 may be configured to simultaneously display information regarding the two electrode units 20.

With reference to FIG. 8A, the start screen 300 includes regions 310, 320, 330, the start button 340, and a stop button 350.

The use state of the electrode unit 20 is displayed in the region 310. The region 310 includes: a graph 311 indicating a relationship between the number of use times of the electrode unit 20 up to the present time point and the upper limit number of times Nth; the number of use times (usable remaining number of times 312) until reaching the upper limit number of times Nth; a cumulative use time period 313 of the electrode unit 20 up to the present time point; and a use start date 314 and a last use date 315 of the electrode unit 20. The number of use times, the cumulative use time period 313, the use start date 314, and the last use date 315 are respectively obtained from the number of times, the cumulative use time period, the start day and time, and the end day and time in the use information shown in FIG. 4A.

In the graph 311, the present number of use times (here, 13 times) is indicated by character information and a bar graph, and the upper limit number of times Nth (here, 14 times) is indicated by character information and a broken line. By referring to the graph 311, the user can intuitively understand the relationship between the present number of use times of the electrode unit 20 and the upper limit number of times Nth. In addition, by referring to the usable remaining number of times 312, the user can accurately understand the remaining number of times the electrode unit 20 can be appropriately used, and by referring to the cumulative use time period 313, the user can understand the total use time period from the first use of the electrode unit 20. Further, by referring to the use start date 314 and the last use date 315, the user can understand the possibility of degradation over time of the electrode unit 20, the relationship with the guarantee period for which the quality is ensured, and the like.

In the region 320, the genuineness/counterfeit determination result regarding the electrode unit 20 obtained in step S205 in FIG. 7 is displayed. By referring to the region 320, the user can understand whether or not the electrode unit 20 attached to the patient is a genuine article. In the region 330, a comment that suggests whether or not the characteristics of the electrode unit 20 can be ensured is displayed. For example, in the region 330, the determination result in step S205 in FIG. 7, a comment indicating a relationship between the number of use times of the electrode unit 20 up to the present time point and the upper limit number of times Nth, and the like are displayed. By referring to the region 330, the user can understand whether or not the characteristics of the electrode unit 20 can be ensured.

The start button 340 is a button for starting operation of the swallowing induction device 1. The stop button 350 is a button for ending operation of the swallowing induction device 1. When the start button 340 has been operated in each of the start screens 300 of the two electrode units 20 attached to the holder unit 10, operation of the swallowing induction device 1 is started, and electric stimulation is provided to the pharynx part of the patient in accordance with a rule determined in advance. Accordingly, swallowing is induced in the patient.

After understanding the information displayed in the regions 310, 320, 330, the user operates either one of the start button 340 and the stop button 350.

For example, when the start screen 300 in FIG. 8A has been displayed, the user understands that there is no problem in either of the genuineness and the use state of the electrode unit 20. In this case, the user may operate the start button 340.

When the start screen 300 in FIG. 8B has been displayed, the user understands that there is a problem about the number of use times although there is no problem about the genuineness of the electrode unit 20. In this case, the user may operate the stop button 350 and replace the electrode unit 20. When the user has determined that the quality of the electrode unit 20 can be ensured, such as when the cumulative use time period 313 is short although the number of use times coincides with the upper limit number of times Nth, the user may operate the start button 340.

When the start screen 300 in FIG. 9A has been displayed, the user understands that the electrode unit 20 is not a genuine article. In this case, the start button 340 is disabled. The user operates the stop button 350 and then replaces the electrode unit 20 which has been determined as "counterfeit" in the genuineness/counterfeit determination. In accordance with the stop button 350 being operated, the start screen 300 of the other electrode unit 20 may be displayed. Accordingly, the user can understand the genuineness/counterfeit determination result and the number of use times of the other electrode unit 20, and can proceed to replacement of the other electrode unit 20 as appropriate. This also applies to a case where the start screen 300 in FIG. 8B has been displayed.

Figure 9B:
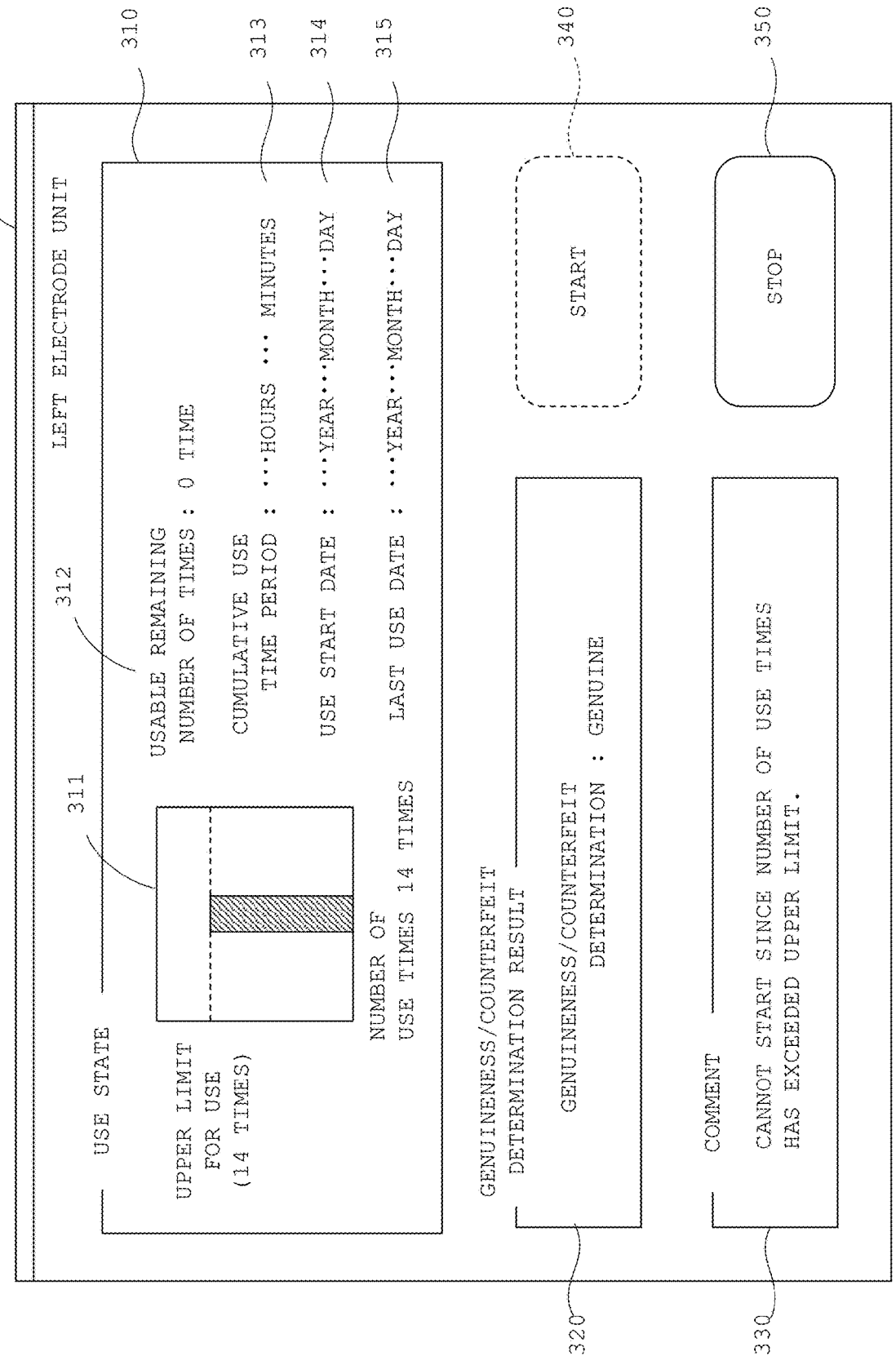
FIG. 9B shows another configuration of the start screen displayed at the time of start of a swallowing induction operation according to Embodiment 1.

In the start screen 300 in FIG. 8B, even when the number of use times of the electrode unit 20 has reached the upper limit number of times Nth, the start button 340 can be operated. However, as shown in FIG. 9B, when the number of use times of the electrode unit 20 has reached the upper limit number of times Nth, the start button 340 may be disabled so as not to be operable. In this case, even when the number of use times of the electrode unit 20 has reached the upper limit number of times Nth, if the cumulative use time period 313 is shorter than a predetermined upper limit time period, the start button 340 may be enabled.

Alternatively, when the number of use times exceeds the upper limit number of times Nth and the difference therebetween is not less than a predetermined number of times, the start button 340 may be disabled so as not to be operable. In this case as well, when the cumulative use time period 313 is shorter than a predetermined upper limit time period, the start button 340 may be enabled.

When the elapsed time period from the use start date 314 has exceeded a predetermined upper limit time period (e.g., the quality guarantee period of the electrode unit 20), or when the elapsed time period from the last use date 315 has exceeded a predetermined upper limit time period (e.g., the quality guarantee period of the electrode unit 20), a message for attracting attention to this fact may be included in the region 330. Further, in such cases, the start button 340 may be disabled.

Figure 10:
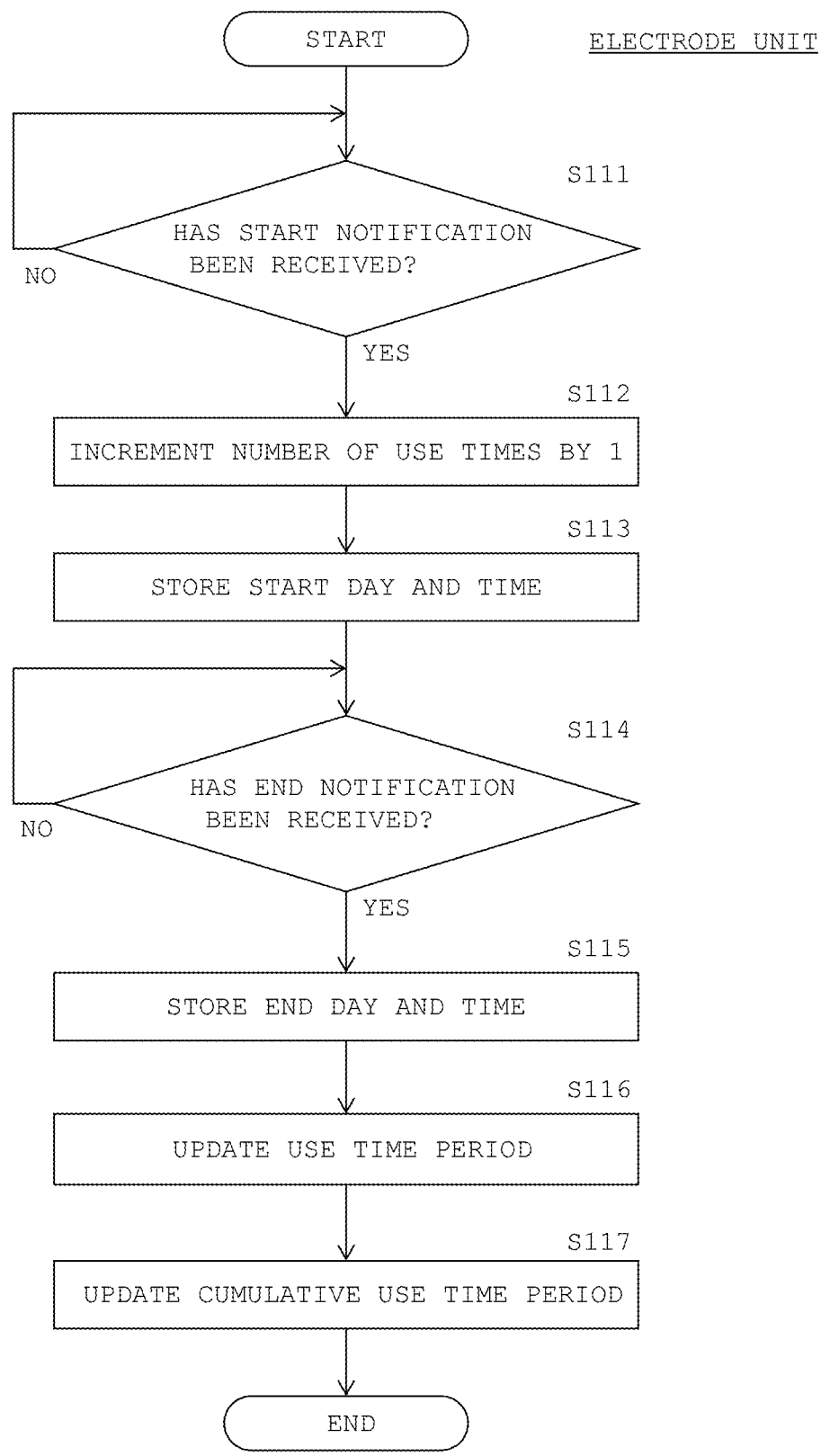
FIG. 10 is a flow chart showing an update process of the use information according to Embodiment 1.

FIG. 10 is a flow chart showing an update process of the use information shown in FIG. 4A.

On the start screen 300 of each electrode unit 20 shown in FIGS. 8A, 8B, when the user has operated the start button 340, the controller 201 of the control unit 3 transmits a start notification to the controller 111 of the holder unit 10. In association with this, the controller 111 transmits the start notification to the controller 121 of the electrode unit 20. Upon receiving the start notification (S111: YES), the controller 121 of the electrode unit 20 adds, to the table of use information, a row of the number of use times in which the number of use times in the present use information is incremented by one (S112), and stores the present day and time in the column of the start day and time of this row (S113). Then, the controller 121 waits for an end notification to be transmitted from the controller 111 of the holder unit 10 (S114).

When operation of the swallowing induction device 1 has been started, the screen displayed on the display input part 203 of the control unit 3 is switched to an operation screen. This operation screen includes a region for indicating an operation state such as the operation time period, and an end button for ending the operation. When the user has operated the end button in the operation screen, an end notification is transmitted from the controller 201 of the control unit 3 to the controller 111 of the holder unit 10. In association with this, the controller 111 transmits the end notification to the controller 121 of the electrode unit 20. The swallowing induction operation may automatically end upon a lapse of a predetermined time period (a default time period, or a time period arbitrarily set by the user) from the start of the swallowing induction operation. In this case, in accordance with the end of the swallowing induction operation, an end notification is transmitted from the control unit 3 to the controller 111 of the holder unit 10, and in association with this, the end notification is transmitted from the controller 111 to the controller 121 of the electrode unit 20.

Upon receiving the end notification, the controller 121 stores the present day and time in the column of the end day and time of the aforementioned row (S115). Further, the controller 121 stores the time difference between the start day and time and the end day and time of this row, into the column of the use time period of this row (S116). Then, the controller 121 stores the time period obtained by adding this time difference to the immediately preceding cumulative use time period, into the column of the cumulative use time period of this row (S117). Then, the update process of the use information in the electrode unit 20 ends.

The process in FIG. 10 is performed in each of the two electrode units 20 attached to the holder unit 10. Accordingly, the pieces of use information retained in the storages 23 of the two electrode units 20 are updated, respectively.

Data accumulated in the control unit 3 through the processes in FIG. 6 and FIG. 7 may be transmitted from the control unit 3 to the server 220 via the second wireless communication part 205 in FIG. 5, and may be managed in the server 220.

Effects of Embodiment 1

According to Embodiment 1, the following effects can be exhibited.

When the use information (the number of use times) regarding the use state of the electrode unit 20 does not satisfy the set condition (the upper limit number of times Nth) for ensuring the characteristics of the electrode unit 20, a control (display of the start screen 300) for restricting use of the electrode unit 20 is performed. Accordingly, when degradation over time is assumed to have occurred in the adhesive members 21 of the electrode unit 20, use of the electrode unit 20 is restricted. Therefore, appropriateness of the swallowing induction operation (medical operation) can be ensured.

The storage 23 storing the use information is disposed in the electrode unit 20. Therefore, even when the electrode unit 20 is combined with a different control unit 3, the use information can be appropriately managed in the electrode unit 20. Thus, the control for restricting use of the electrode unit 20 can be appropriately executed in the control unit 3.

Whether or not the use information (the number of use times) satisfies the set condition (the upper limit number of times Nth) is determined on the electrode unit 20 side, and the determination result is transmitted to the control unit 3. Accordingly, the processing burden in the control unit 3 can be reduced. Whether or not the use information (the number of use times) satisfies the set condition (the upper limit number of times Nth) may be determined on the control unit 3 side. In this case, the electrode unit 20 only needs to read out the use information from the storage 23 and to transmit the use information to the control unit 3.

Further, the confirmation information for confirming that the electrode unit 20 is a genuine article is further stored in the storage 23 of the electrode unit 20. Then, on the basis of the fact that the electrode unit 20 being a genuine article has not been able to be confirmed by the confirmation information, the control unit 3 executes a control (disabling the start button 340 on the start screen 300) for restricting use of the electrode unit 20. Accordingly, use of a poor-quality imitation article of the electrode unit 20 can be prevented. Therefore, appropriateness of the swallowing induction operation can be more reliably ensured.

In the start screen 300 shown FIG. 9B, on the basis of the fact that the use information (the number of use times) does not satisfy the set condition (the upper limit number of times Nth), the start button 340 is disabled, and the swallowing induction operation is stopped. That is, when degradation over time is assumed to have occurred in the electrode unit 20, the swallowing induction operation itself is stopped. Therefore, the swallowing induction operation can be prevented from being performed by the electrode unit 20 where degradation has occurred, and appropriateness of the swallowing induction operation can be reliably ensured.

As shown in FIG. 8B, on the basis of the fact that the use information (the number of use times) does not satisfy the set condition (the upper limit number of times Nth), the control unit 3 causes the display input part 203 to display report information (the message in the region 330) for inhibiting use of the electrode unit 20. Thus, by referring to the report information (the message in the region 330), the user such as a doctor can avoid use of the degraded electrode unit 20. Therefore, appropriateness of the swallowing induction operation can be ensured.

As shown in FIG. 8A to FIG. 9B, the control unit 3 causes the display input part 203 to display information (the graph 311, the usable remaining number of times 312, the message in the region 330) indicating the relationship between the use information (the number of use times) and the set condition (the upper limit number of times Nth). Accordingly, by referring to these pieces of information displayed on the display input part 203, the user such as a doctor can understand the state of degradation over time of the electrode unit 20, and can take measures such as replacing the electrode unit 20 as appropriate. Therefore, the swallowing induction operation can be more appropriately conducted.

Embodiment 2

Figure 11A:
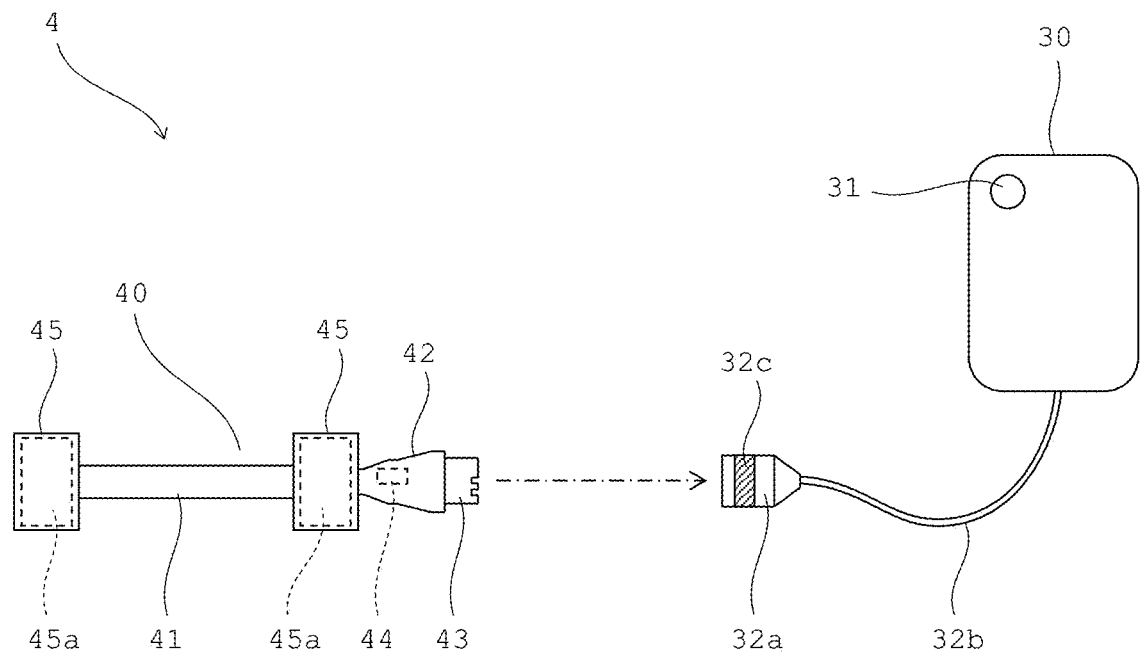
FIG. 11A shows a configuration of a respiration detection device according to Embodiment 2.
Figure 11B:
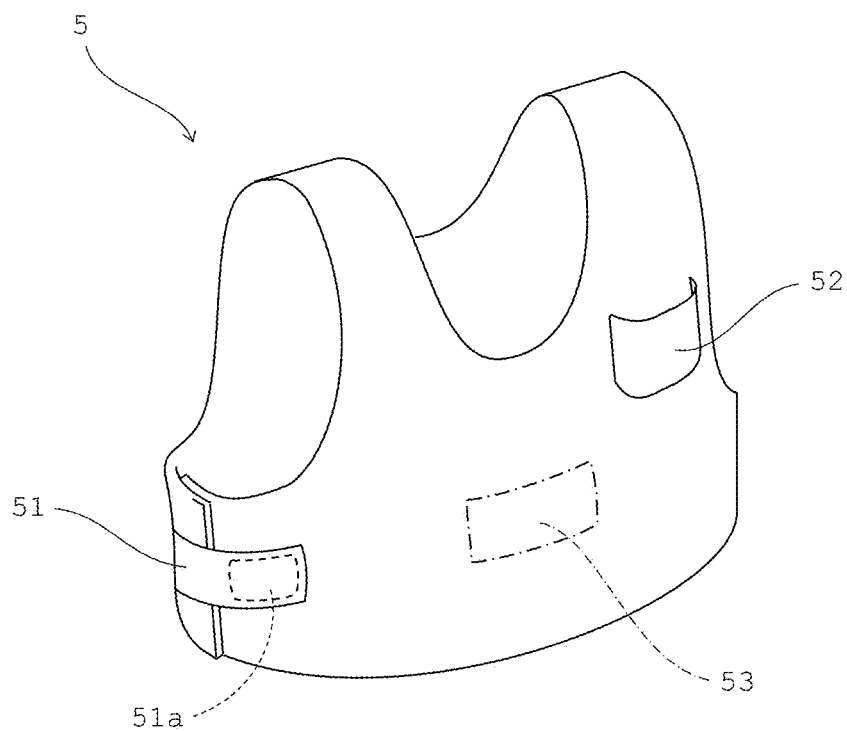
FIG. 11B shows a configuration of a vest for attaching the respiration detection device to a patient, according to Embodiment 2.

FIG. 11A shows a configuration of a respiration detection device 4 according to Embodiment 2. FIG. 11B shows a configuration of a vest 5 for attaching the respiration detection device 4 to a patient.

In Embodiment 2, the respiration detection device 4 for detecting respiration of the patient is further included in the swallowing induction device 1. The swallowing induction device 1 controls the timing of electric stimulation provided by each electrode unit 20 on the basis of respiration of the patient detected by the respiration detection device 4. Specifically, the electrode unit 20 is controlled such that the entire period of the electric stimulation is included in an expiration period of the patient. Accordingly, swallowing is induced in the patient at an appropriate timing when aspiration does not occur, whereby the symptom of aspiration in the patient is improved.

In Embodiment 2, other than the electrode unit 20, a respiration detection unit 40 corresponds to an "attachment unit" described in the claims. However, Embodiment 2 described below is merely a configuration example obtained through implementation of the present invention, and does not limit the invention according to the claims in any way.

As shown in FIG. 11A, the respiration detection device 4 includes a body unit 30 and the respiration detection unit 40.

The body unit 30 has a shape that is housed in a pocket 52 of the vest 5. The shape of the body unit 30 is a shape of a rectangular parallelepiped having rounded corners. A power supply such as a battery and a circuit board for driving the respiration detection unit 40 are housed in the body unit 30. A power supply button 31 is disposed on the obverse surface of the body unit 30. A cable 32b is drawn from the body unit 30, and a connector 32a is provided to the leading end of this cable 32b. The cable 32b is connected to the circuit board housed in the body unit 30. As indicated by the arrow of an alternate long and short dash line in FIG. 11A, a terminal 43 of the respiration detection unit 40 is inserted into the connector 32a.

The connector 32a is provided with a structure for fixing the inserted terminal 43. For example, a lever 32c for switching between fixation and release is provided to the outer-side face of the connector 32a. When the lever 32c is lifted from the outer-side face of the connector 32a, attachment/detachment of the terminal 43 with respect to the connector 32a is enabled. In this state, when the terminal 43 is inserted into the connector 32a, and then the lever 32c is pushed down to the outer-side face of the connector 32a, the terminal 43 is fixed to the connector 32a.

The respiration detection unit 40 includes a stretch sensor 41 in a strip shape for detecting expansion and contraction, of the torso of the patient, that are associated with respiration. The stretch sensor 41 is configured such that the electrostatic capacitance changes in accordance with stretch and contraction thereof, for example. The stretch sensor 41 is formed from a rubber material, for example.

A grip part 42 is attached to one end part of the stretch sensor 41, and the terminal 43 protrudes from the grip part 42. A circuit board is built in the grip part 42, and the terminal 43 is connected to this circuit board. This circuit board is also connected to the stretch sensor 41. A storage 44 implemented by an EEPROM, for example, is mounted to this circuit board. As described later, the storage 44 stores use information regarding the use state over time of the stretch sensor 41, confirmation information for confirming that the stretch sensor 41 is a genuine article, and the like.

Further, wide base parts 45 are respectively provided to both ends of the stretch sensor 41. A fastening part 45a implemented by a Hook-and-Loop fastener is provided to the reverse surface of each base part 45. The fastening parts 45a are for attaching the respiration detection unit 40 to an attachment region 53 of the vest 5. Each fastening part 45a serves as one side of the Hook-and-Loop fastener, and the other side of the Hook-and-Loop fastener is provided to the attachment region 53. Other than this, the stretch sensor 41 may be adhered to a stretchable cloth, and this cloth may be attached to the attachment region 53 of the vest 5 by a Hook-and-Loop fastener or the like.

As shown in FIG. 11B, the vest 5 has a jacket-like shape that can be worn on the upper half of the body of the patient. The vest 5 is formed from a stretchable material. One side part of the vest 5 is openable/closable, and a belt 51 is provided to this side part. A fastening part 51a implemented by a Hook-and-Loop fastener is provided to the reverse surface of an end part of the belt 51. A Hook-and-Loop fastener is also provided to the obverse surface of the vest 5 to be overlapped by the fastening part 51a. When the end part of the belt 51 is laid on the obverse surface of the vest 5, the fastening part 51a is temporarily fastened to the vest 5. As a result, the side part of the vest 5 is closed.

The pocket 52 is provided to the vicinity of the chest part of the vest 5. A hole for allowing the connector 32a and the cable 32b to pass therethrough is provided to a bottom part of the pocket 52. Further, the attachment region 53 is provided to the vicinity of the belly part of the vest 5. As described above, a Hook-and-Loop fastener is provided to the attachment region 53.

Figure 12:
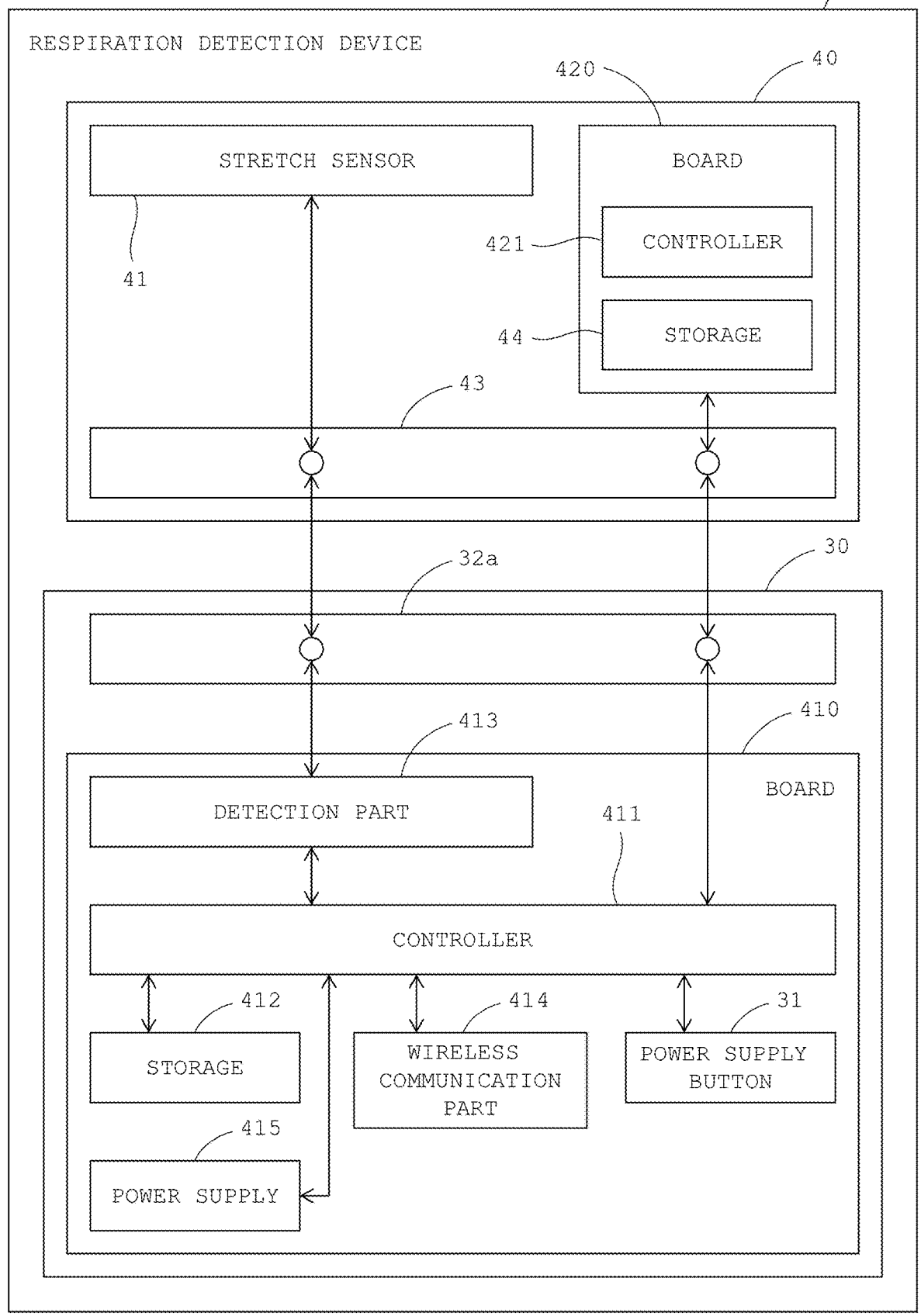
FIG. 12 is a block diagram showing a circuit configuration of the respiration detection device according to Embodiment 2.

FIG. 12 is a block diagram showing a circuit configuration of the respiration detection device 4.

The body unit 30 and the respiration detection unit 40 include circuit boards 410, 420, respectively. As described above, the circuit board 410 is built in the body unit 30. The circuit board 420 is built in the grip part 42 of the respiration detection unit 40. These circuit boards 410, 420 are connected to each other by the terminal 43 being connected to the connector 32a.

The circuit board 410 of the body unit 30 has mounted thereon a controller 411, a storage 412, a detection part 413, a wireless communication part 414, and a power supply 415. Other than these, the power supply button 31 shown in FIG. 11 is also provided on the circuit board 410.

The controller 411 is implemented by a microcomputer, for example, and controls components in accordance with a program stored in the storage 412. The storage 412 is implemented by a ROM, a RAM, etc., and stores a program for controlling components. The storage 412 is used as a work area when the controller 411 controls components.

The detection part 413 provides voltage to both ends of the stretch sensor 41, detects change in voltage according to stretch and contraction of the stretch sensor 41, and outputs the detection result to the controller 411. The wireless communication part 414 performs wireless communication with the control unit 3 shown in FIG. 5 in accordance with control from the controller 411. The power supply 415 includes a battery and supplies a power supply voltage to circuit parts of the circuit boards 410, 420. The power supply voltage is supplied to the circuit board 420 on the respiration detection unit 40 side via the cable 32b in FIG. 11.

The circuit board 420 of the respiration detection unit 40 has mounted thereon a controller 421 and the storage 44. The controller 421 is implemented by a microcomputer, for example, and controls components in accordance with a program stored in the storage 44. The controller 421 has a clock function of clocking the present day and time. The storage 44 is implemented by a ROM, a RAM, etc., and stores a program for controlling components. The storage 44 is used as a work area when the controller 421 controls components.

The storage 44 includes a nonvolatile memory (EEPROM) for which data is writable and erasable. The storage 44 stores, into this nonvolatile memory, use information regarding the use state of the respiration detection unit 40. In addition, the storage 44 stores, into a predetermined area other than the writing area of the use information in this nonvolatile memory, confirmation information for confirming that the respiration detection unit 40 is a genuine article, i.e., that the respiration detection unit 40 has been manufactured by an appropriate manufacturer. The configurations of the use information and the confirmation information are the same as those shown in FIGS. 4A, 4B.

FIG. 13 shows a state where the electric stimulation device 2 and the respiration detection device 4 have been attached to the patient.

The vest 5 is attached to the patient and the side part of the vest 5 is closed by the belt 51. At this time, the belt 51 is laid on the vest 5 such that the vicinity of the chest of the patient is slightly compressed. Next, the body unit 30 is housed in the pocket 52, and the terminal 43 of the respiration detection unit 40 is connected to the connector 32a. Then, in a state where the patient has completely exhaled, the respiration detection unit 40 is attached to the attachment region 53 of the vest 5. Accordingly, the respiration detection device 4 is attached to the patient. Then, by a method similar to that in Embodiment 1 above, the electric stimulation device 2 is attached to the patient. In this manner, attachment of the electric stimulation device 2 and the respiration detection device 4 to the patient is completed. In the state shown in FIG. 13, when the patient breathes, the stretch sensor 41 stretches and contracts in accordance with expansion and contraction of the torso of the patient. Accordingly, respiration can be detected.

The user such as a doctor operates the power supply button 11 of the holder unit 10 and operates the power supply button 31 of the body unit 30. Further, similar to Embodiment 1 above, the user starts an application program (the program 202a in FIG. 5), for induction of swallowing, installed in the control unit 3. Accordingly, a wireless communication path is established between the control unit 3, and the electric stimulation device 2 and the respiration detection device 4.

Then, the processes in FIG. 6 and FIG. 7 are respectively performed in the controller 121 of the electrode unit 20 and the controller 201 of the control unit 3. Accordingly, the start screen 300 shown in FIG. 8A to FIG. 9A is displayed on the display input part 203 of the control unit 3. The user determines, with reference to the displayed start screen 300, whether or not the characteristics of the electrode unit 20 are ensured, and operates the start button 340 or the stop button 350 in accordance with the determination result.

Further, in Embodiment 2, processes similar to those in FIG. 6 and FIG. 7 are respectively performed in the controller 421 of the respiration detection unit 40 and the controller 201 of the control unit 3. Here, the upper limit number of times Nth in step S105 in FIG. 6 is set to a number of times that can be assumed to be able to ensure the characteristics of the stretch sensor 41. The stretch sensor 41 is degraded through repetition of stretch and contraction thereof. The upper limit number of times Nth is set in assumption of this degradation. For example, when one swallowing induction operation is performed for about 30 minutes, the upper limit number of times Nth is set to about 100 times.

Processes similar to those in FIG. 6 and FIG. 7 are performed with respect to the respiration detection unit 40, whereby a start screen similar to the start screen 300 shown in FIG. 8A to FIG. 9A is displayed on the display input part 203 of the control unit 3. This start screen is displayed in accordance with the start button 340 being operated on the start screen 300 displayed with respect to the electrode unit 20, for example. This start screen includes regions (regions similar to the regions 310, 320, 330) for respectively displaying the use state, a genuineness/counterfeit determination result, and a comment that suggests whether or not the characteristics can be ensured, with respect to the respiration detection unit 40. This start screen further includes buttons respectively corresponding to the start button 340 and the stop button 350.

The user determines, with reference to the displayed start screen, whether or not the characteristics of the respiration detection unit 40 are ensured, and operates the start button or the stop button in accordance with the determination result. When the start button 340 is operated on the start screen 300 displayed with respect to the electrode unit 20, and further, the start button is operated on the start screen displayed with respect to the respiration detection unit 40, a swallowing induction operation is started.

In this case, the controller 201 of the control unit 3 detects respiration of the patient on the basis of a signal according to stretch and contraction of the stretch sensor 41 and received from the respiration detection unit 40, and controls the electric stimulation device 2 on the basis of the detection result of the respiration. Specifically, the controller 201 drives the electric stimulation device 2 such that the entire period of the electric stimulation is included in the expiration period of the patient. Accordingly, swallowing can be promoted at an appropriate timing.

When the swallowing induction operation has been started in this manner, the process shown in FIG. 10 is performed in the controller 121 of the electrode unit 20, and further, a process similar to that in FIG. 10 is performed in the controller 421 of the respiration detection unit 40. Accordingly, the use information stored in the storage 23 of the electrode unit 20 is updated, and the use information stored in the storage 44 of the respiration detection unit 40 is updated.

Effects of Embodiment 2

In Embodiment 2 as well, effects similar to those in Embodiment 1 above can be exhibited.

Further, in Embodiment 2, when the use information (the number of use times) of the respiration detection unit 40 does not satisfy the set condition (the upper limit number of times Nth), i.e., when degradation over time is assumed to have occurred in the stretch sensor 41, a control (display of a start screen similar to the start screen 300) for restricting use of the respiration detection unit 40 is performed. Accordingly, appropriateness of the swallowing induction operation can be ensured.

Embodiment 3

Embodiment 3 has been made by applying the present invention to a swallowing monitoring device 6 that monitors a swallowing movement of a patient, and to a swallowing diagnosis device 7 for diagnosing a risk of aspiration of the patient by using the swallowing monitoring device 6.

In Embodiment 3, the swallowing monitoring device 6 or the swallowing diagnosis device 7 corresponds to a "swallowing medical device" described in the claims, and the respiration detection unit 40 and a displacement detection unit 60 correspond to an "attachment unit" described in the claims. However, Embodiment 3 described below is merely a configuration example obtained through implementation of the present invention, and does not limit the invention according to the claims in any way.

Figure 14:
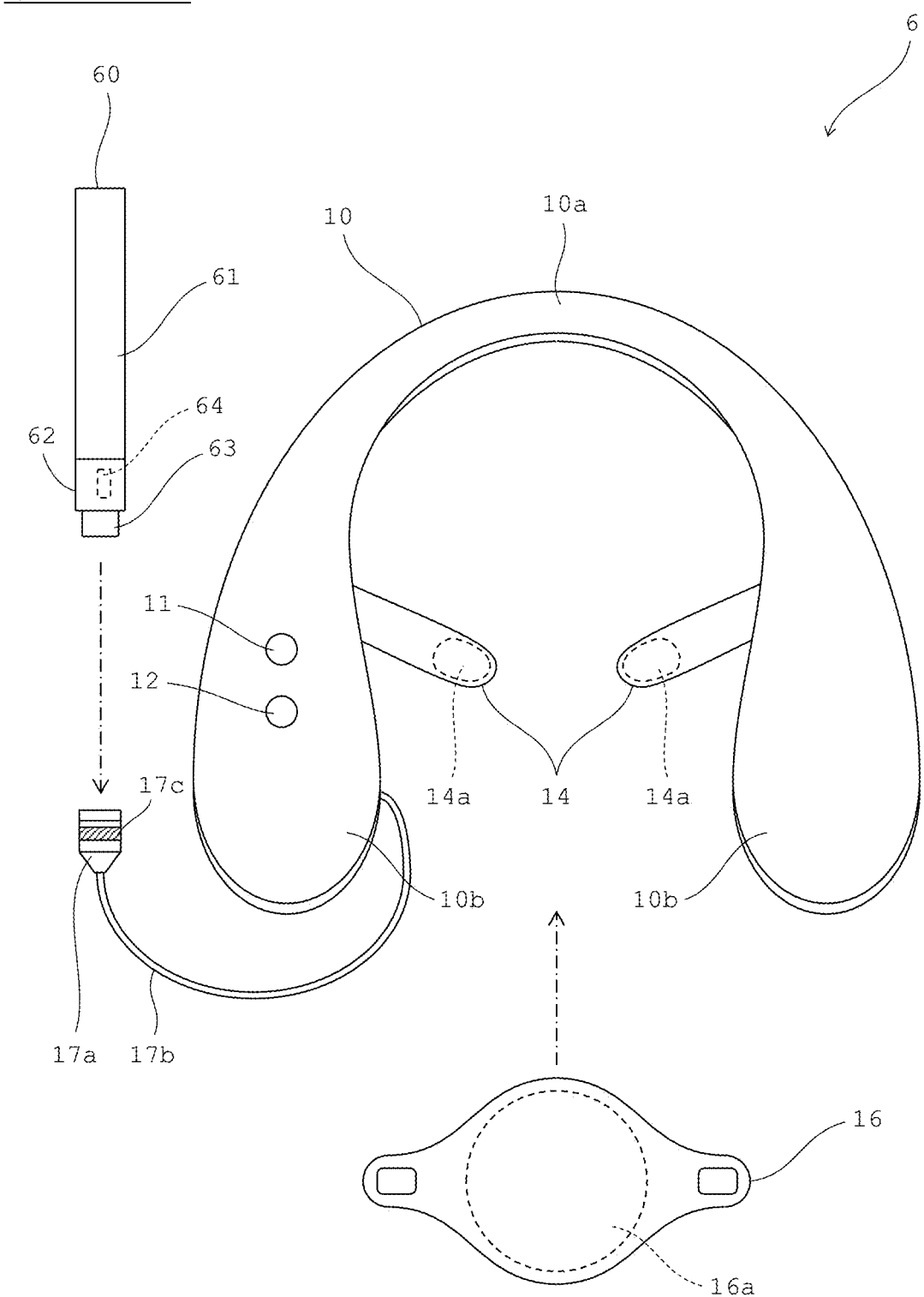
FIG. 14 shows a configuration of a swallowing monitoring device according to Embodiment 3.

FIG. 14 shows a configuration of the swallowing monitoring device 6 according to Embodiment 3.

As shown in FIG. 14, the swallowing monitoring device 6 includes a holder unit 10 that has a substantially same configuration as that in FIG. 1. However, in Embodiment 3, the press members 13 in FIG. 1 are omitted from the holder unit 10, and instead, a press member 16 is included in the holder unit 10. In addition, a cable 17b is drawn from only one of two end parts 10b, and a connector 17a is attached to the leading end of this cable 17b. The configuration of the connector 17a is similar to that of the connector 15a in FIG. 1. A terminal 63 of the displacement detection unit 60 can be attached/detached to/from a connector 17a by operating a lever 17c.

The press member 16 is for pressing a displacement sensor 61 of the displacement detection unit 60 to the larynx part of the patient when the holder unit 10 has been attached to the patient. The press member 16 is formed in a bag shape by using a stretchable cloth, for example, and a cushioning member 16a such as microbeads is enclosed inside this bag. Fastening parts serving as one side of a Hook-and-Loop fastener are respectively provided on the obverse surfaces of left and right protrusions of the press member 16. The fastening parts are joined to fastening parts 14a implemented by the other Hook-and-Loop fastener provided to the reverse surfaces of the belts 14.

The displacement detection unit 60 includes the displacement sensor 61 in a strip shape, a grip part 62, the terminal 63, and a storage 64. The displacement sensor 61 is a piezoelectric sensor (PVDF polymer piezoelectric body) in a film shape, for example. The displacement sensor 61 outputs a voltage according to a displacement.

The grip part 62 is attached to one end part of the displacement sensor 61, and the terminal 63 protrudes from this grip part 62. A circuit board is built in the grip part 62, and the terminal 63 is connected to this circuit board. This circuit board is also connected to the displacement sensor 61. This circuit board has mounted thereon the storage 64 implemented by an EEPROM, for example. As described later, the storage 64 stores use information regarding the use state over time of the displacement sensor 61, confirmation information for confirming that the displacement sensor 61 is a genuine article, and the like.

Figure 15:
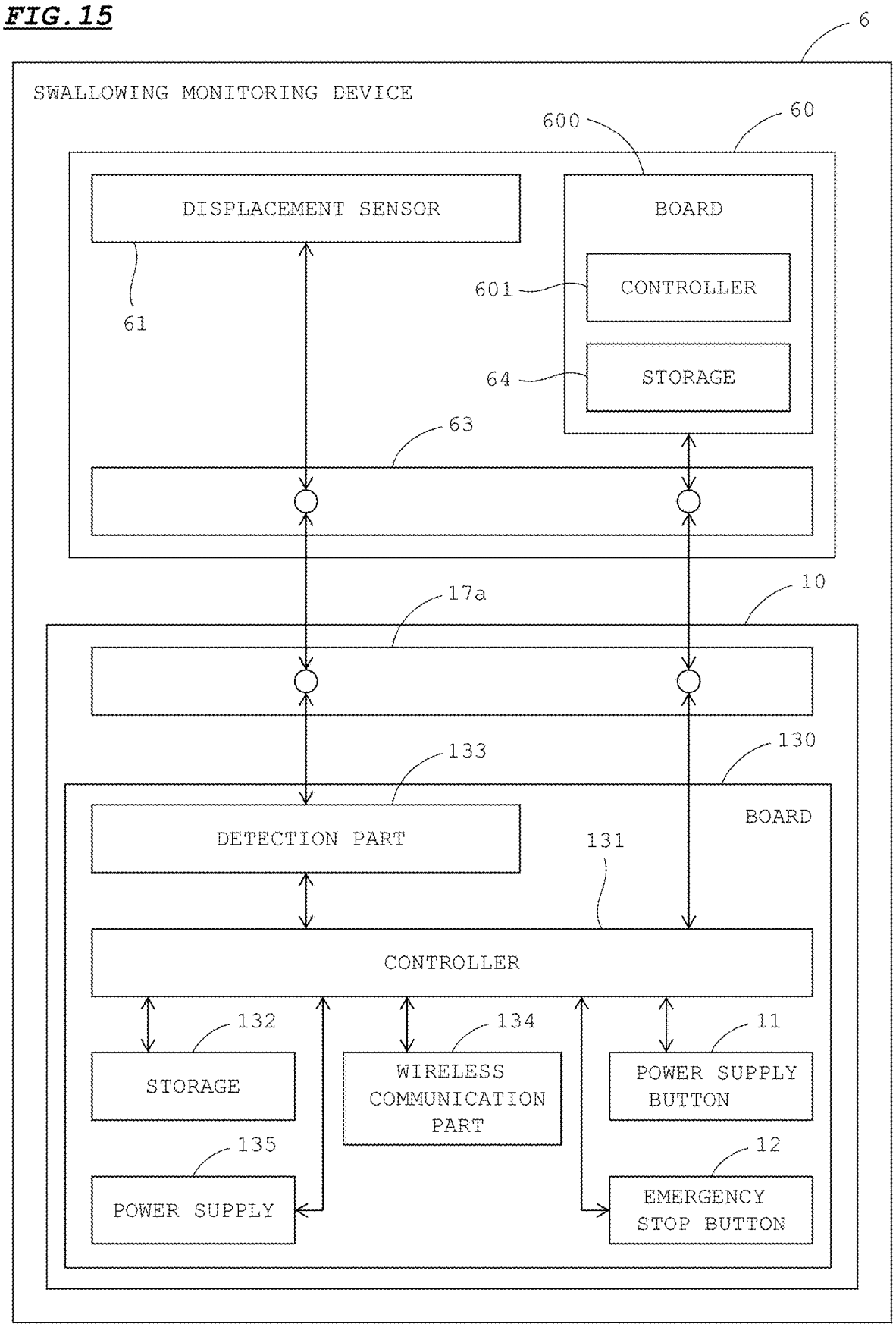
FIG. 15 is a block diagram showing a circuit configuration of the swallowing monitoring device according to Embodiment 3.

FIG. 15 is a block diagram showing a circuit configuration of the swallowing monitoring device 6.

The holder unit 10 and the displacement detection unit include circuit boards 130, 600, respectively. Similar to Embodiment 1 above, the circuit board 130 is built in on the inner side with respect to the power supply button 11 and the emergency stop button 12 of the holder unit 10. The circuit board 600 is built in the grip part 62 of the displacement detection unit 60. These circuit boards 130, 600 are connected to each other by the terminal 63 being connected to the connector 17a.

The circuit board 130 of the holder unit 10 has mounted thereon a controller 131, a storage 132, a detection part 133, a wireless communication part 134, and a power supply 135. Other than these, the power supply button 11 and the emergency stop button 12 shown in FIG. 15 are also provided on the circuit board 130. Configurations of components other than the emergency stop button 12 are similar to the configurations of components provided on the circuit board 410 in FIG. 12 shown in Embodiment 2 above. The detection part 133 provides voltage to the displacement sensor 61, detects change in voltage according to displacement of the displacement sensor 61, and outputs the detection result to the controller 131.

The circuit board 600 of the displacement detection unit 60 has mounted thereon a controller 601 and the storage 64. The controller 601 is implemented by a microcomputer, for example, and controls components in accordance with a program stored in the storage 64. The controller 601 has a clock function of clocking the present day and time. The storage 64 is implemented by a ROM, a RAM, etc., and stores a program for controlling components. The storage 64 is used as a work area when the controller 601 controls components.

The storage 64 includes a nonvolatile memory (EEPROM) for which data is writable and erasable. The storage 64 stores, into this nonvolatile memory, use information regarding the use state of the displacement detection unit 60. In addition, the storage 64 stores, into a predetermined area other than the writing area of the use information in this nonvolatile memory, confirmation information for confirming that the displacement detection unit 60 is a genuine article, i.e., that the displacement detection unit 60 has been manufactured by an appropriate manufacturer. The configurations of the use information and the confirmation information are the same as those shown in FIGS. 4A, 4B.

FIG. 16 shows a state where the respiration detection device 4 and the swallowing monitoring device 6 have been attached to the patient.

The configuration of the respiration detection device 4 is similar to that in Embodiment 2 above. The respiration detection device 4 is attached to the patient by a method similar to that in Embodiment 2 above. Then, the swallowing monitoring device 6 is attached to the patient. First, the displacement detection unit 60 is connected to the holder unit 10. Next, the holder unit 10 is wound around the neck of the patient. Then, the displacement sensor 61 is laid on the larynx part of the patient, and further, the press member 16 is laid on the obverse surface of the displacement sensor 61. In this state, the two belts 14 are overlaid with each other, whereby the press member 16 is pressed by the belts 14. Accordingly, the displacement sensor 61 is attached to the larynx part of the patient.

In Embodiment 3, a program 202a for diagnosing aspiration by monitoring swallowing of the patient is installed in the storage 202 of the control unit 3.

The user such as a doctor operates the power supply button 11 of the holder unit 10 and operates the power supply button 31 of the body unit 30. Further, the user starts an application program (the program 202a), for diagnosing swallowing, installed in the control unit 3. Accordingly, a wireless communication path is established between the control unit 3, and the respiration detection device 4 and the swallowing monitoring device 6.

Then, similar to Embodiment 2 above, processes similar to those in FIG. 6 and FIG. 7 are respectively performed in the controller 421 of the respiration detection unit 40 and the controller 201 of the control unit 3. Accordingly, a start screen similar to the start screen 300 shown in FIG. 8A to FIG. 9A is displayed on the display input part 203 of the control unit 3. The user determines, with reference to the displayed start screen, whether or not the characteristics of the respiration detection unit 40 are ensured, and operates the start button or the stop button in accordance with the determination result.

Further, in Embodiment 3, processes similar to those in FIG. 6 and FIG. 7 are respectively performed in the controller 601 of the displacement detection unit 60 and the controller 201 of the control unit 3. Here, the upper limit number of times Nth in step S105 in FIG. 6 is set to a number of times that can be assumed to be able to ensure the characteristics of the displacement sensor 61. The displacement sensor 61 is degraded through repetition of displacement thereof. The upper limit number of times Nth is set in assumption of this degradation. For example, when one swallowing induction operation is performed for about 30 minutes, the upper limit number of times Nth is set to about 100 times.

Processes similar to those in FIG. 6 and FIG. 7 are performed with respect to the displacement detection unit 60, whereby a start screen similar to the start screen 300 shown in FIG. 8A to FIG. 9A is displayed on the display input part 203 of the control unit 3. This start screen is displayed in accordance with the start button being operated on the start screen with respect to the respiration detection unit 40, for example. This start screen includes regions (regions similar to the regions 310, 320, 330) for respectively displaying the use state, a genuineness/counterfeit determination result, and a comment that suggests whether or not the characteristics can be ensured, with respect to the displacement detection unit 60. This start screen further includes buttons respectively corresponding to the start button 340 and the stop button 350.

The user determines, with reference to the displayed start screen, whether or not the characteristics of the respiration detection unit 40 are ensured, and operates the start button or the stop button in accordance with the determination result. When the start button is operated on the start screen displayed with respect to the respiration detection unit 40, and further, the start button is operated on the start screen displayed with respect to the displacement detection unit 60, a swallowing diagnosis operation is started.

In this case, the controller 201 of the control unit 3 detects respiration of the patient on the basis of a signal according to stretch and contraction of the stretch sensor 41 and received from the respiration detection unit 40, and detects swallowing of the patient on the basis of a signal according to displacement of the displacement sensor 61 and received from the displacement detection unit 60. Then, the controller 201 determines a risk of aspiration of the patient on the basis of whether or not the detected swallowing timing is appropriate for respiration. Specifically, when the timings before and after swallowing are in an expiration period, the controller 201 determines that the swallowing is appropriate. When either one of the timings before and after swallowing is in an inspiration period, the controller 201 determines that the swallowing is inappropriate. Then, for each swallowing, the controller 201 causes the display input part 203 to display a determination result as to whether or not the swallowing is appropriate, as information that indicates the presence or absence of a risk of aspiration.

When the swallowing monitoring operation and the swallowing diagnosis operation have been started in this manner, a process similar to that in FIG. 10 is performed in the controller 421 of the respiration detection unit 40 as in Embodiment 2 above, and further, a process similar to that in FIG. 10 is performed in the controller 601 of the displacement detection unit 60. Accordingly, the use information stored in the storage 44 of the respiration detection unit 40 is updated, and the use information stored in the storage 64 of the displacement detection unit 60 is updated.

In a case where the control unit 3 is used at the patient's house and the swallowing monitoring operation and the swallowing diagnosis operation are performed, results of these operations are stored into the storage 202 of the control unit 3, together with the date. On a later date, when the patient receives medical care in a medical institution, the patient brings the control unit 3 to a medical worker such as a doctor, and presents, to the doctor, results of the swallowing monitoring operation and the swallowing diagnosis operation performed in the patient's house. Accordingly, the doctor can appropriately provide medical care to the patient.

The doctor transfers information regarding the swallowing diagnosis result in the control unit 3 to a terminal or the like in the medical institution, as appropriate.

Alternatively, information regarding swallowing diagnosis results accumulated in the control unit 3 may be transmitted to the server 220 via the second wireless communication part 205 in FIG. 5, to be managed in the server 220. In this case, the control unit 3 transmits, to the server 220, information regarding each diagnosis result together with the ID information of the patient and the diagnosis day and time. The server 220 stores, into a database, the diagnosis day and time and the diagnosis result in association with the ID information of the patient.

Effects of Embodiment 3

Similar to Embodiment 2 above, in Embodiment 3 as well, use of the respiration detection unit 40 is restricted when the characteristics of the respiration detection unit 40 are not ensured. Therefore, appropriateness of the swallowing monitoring operation and the swallowing diagnosis operation can be ensured.

Further, in Embodiment 3, when the use information (the number of use times) of the displacement detection unit 60 does not satisfy the set condition (the upper limit number of times Nth), i.e., when degradation over time is assumed to have occurred in the displacement sensor 61, a control (display of a start screen similar to the start screen 300) for restricting use of the displacement detection unit 60 is performed. Accordingly, appropriateness of the swallowing monitoring operation and the swallowing diagnosis operation can be ensured.

<Modification>

Embodiments of the present invention have been described. However, the present invention is not limited to the embodiments above, and various modifications can be made to the embodiments of the present invention.

For example, in Embodiments 1 to 3 above, whether or not the characteristics of each electrode unit 20, the respiration detection unit 40, and the displacement detection unit 60 are ensured is determined on the basis of whether or not the number of use times in the use information exceeds the upper limit number of times. However, in addition to this or instead of this, whether or not the characteristics of the electrode unit 20, the respiration detection unit 40, and the displacement detection unit 60 can be ensured may be determined on the basis of another type of information included in the use information. For example, whether or not the characteristics of the electrode unit 20, the respiration detection unit 40, and the displacement detection unit 60 can be ensured may be determined on the basis of whether or not the cumulative use time period included in the use information exceeds an upper limit time period set in advance. Alternatively, whether or not the characteristics of the electrode unit 20, the respiration detection unit 40, and the displacement detection unit 60 can be ensured may be determined on the basis of whether or not an elapsed time period from the start of use or an elapsed time period from the last use has exceeded an upper limit time period set in advance. In a case where the date of manufacture or the shipping date are managed, whether or not the characteristics of the electrode unit 20, the respiration detection unit 40, and the displacement detection unit 60 can be ensured may be determined on the basis of whether or not an elapsed time period from these dates exceeds an upper limit time period set in advance.

In Embodiments 1 to 3 above, the start screen 300 in FIG. 8A to FIG. 9B is displayed on the basis of the confirmation information and the use information. However, the configuration of the start screen 300 is not limited thereto. For example, the graph 311 may be a graph in another form such as a line graph or a pie graph, and the number of use times by which the upper limit number of times Nth is exceeded may be included in the region 310. In addition, when the number of use times has reached the upper limit number of times Nth, the background color, the frame line, etc., of the region 330, the graph 311, or the like may be displayed in an emphasized manner in order to attract attention, or alternatively, the usable remaining number of times 312 may be displayed in characters in red or the like so as to be emphasized. Similarly, when the genuineness/counterfeit determination result is "counterfeit", the background color, the frame line, etc., of the region 320 may be displayed in an emphasized manner in order to attract attention. The region 310 may be omitted from the start screen 300 shown in FIG. 8A to FIG. 9B, or the region 330 may be omitted from the start screen 300. When the genuineness/counterfeit determination result is "counterfeit", the start button 340 need not necessarily be disabled, and information indicating the fact may only be displayed in the region 330.

In Embodiments 1 to 3 above, after the electrode unit 20, the respiration detection unit 40, and the displacement detection unit 60 are attached to the patient, processes in FIG. 6 and FIG. 7 are executed. However, before the electrode unit 20, the respiration detection unit 40, and the displacement detection unit 60 are attached to the patient, the electrode unit 20, the respiration detection unit 40, the displacement detection unit 60, and the control unit 3 may be operated to execute the processes in FIG. 6 and FIG. 7.

In Embodiments 1 to 3 above, at the time of start of operation of each device, the processes in FIG. 6 and FIG. 7 are executed, and whether or not the electrode unit 20, the respiration detection unit 40, and the displacement detection unit 60 are appropriate is determined. Further, whether or not the electrode unit 20, the respiration detection unit 40, and the displacement detection unit 60 are appropriate may be determined during operation of the devices.

In Embodiments 1 to 3 above, in the genuineness/counterfeit determination performed in step S205 in FIG. 7, the control unit 3 inquires of the server 220 about the presence or absence of double registration of the serial number. However, this inquiry may be omitted, and whether the electrode unit 20, the respiration detection unit 40, and the displacement detection unit 60 are genuine or counterfeit may be determined only on the basis of whether or not the serial number can be decrypted using the encryption key and whether or not the number of digits of the decrypted serial number is appropriate.

Figure 17:
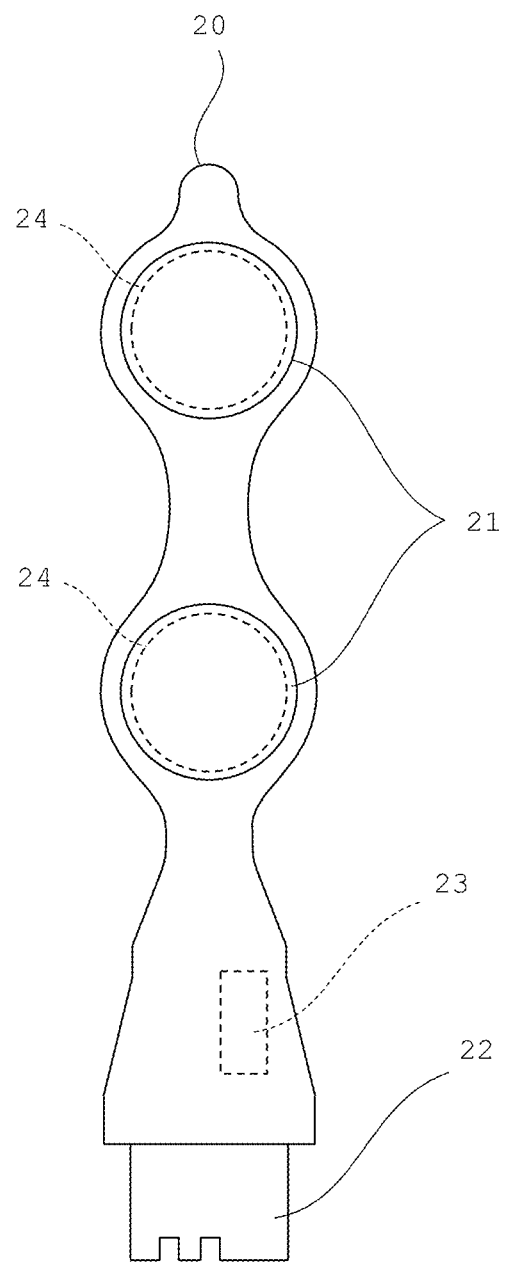
FIG. 17 shows a configuration of an electrode unit according to a modification.

The configurations of the electrode unit 20, the respiration detection unit 40, and the displacement detection unit 60 are not limited to those shown in Embodiments 1 to 3 above, and may be other configurations as long as electric stimulation can be appropriately provided to the pharynx part of the patient and respiration of the patient and displacement of the larynx part can be appropriately detected. For example, as shown in FIG. 17, the length of the electrode unit 20 may be reduced. In this modification, costs of the electrode unit 20 can be reduced. The respiration detection unit 40 may be configured to detect the respiration pressure of the patient by means of a nasal cannula.

Since the electrode unit 20, the respiration detection unit 40, and the displacement detection unit 60 are directly touched by hands, the circuit boards of these units may be provided with static electricity protection circuits for protecting the controllers 121, 421, 601 and the storages 23, 44, 64 from static electricity. In this case, for example, a static electricity absorbing element such as a varistor for absorbing static electricity is inserted between the signal line and a ground line or shield line of the controller 121, 421, 601 and the storage 23, 44, 64. A static electricity protection circuit may be provided at least to the controller 121, 421, 601.

In Embodiment 1 above, determination as to whether or not the use information (the number of use times) satisfies the set condition (the upper limit number of times Nth) is performed in the electrode unit 20. However, as described above, this determination may be performed on the control unit 3 side.

Figure 18:
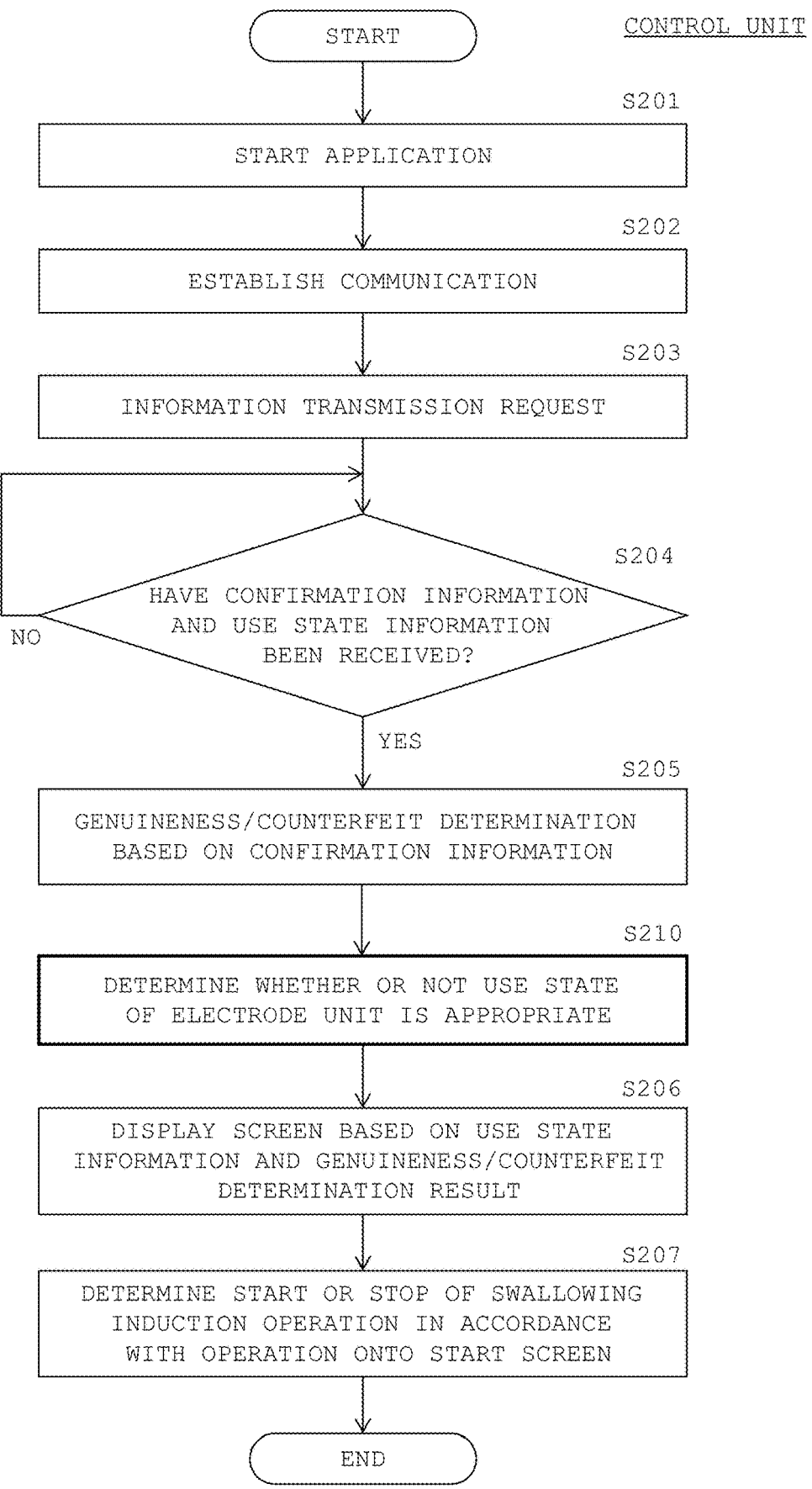
FIG. 18 is a flow chart showing a control to be executed by the controller of the control unit when a swallowing induction operation is started, according to another modification.

In this case, steps S104 to S107 are omitted from the flow chart in FIG. 6, and the use information is transmitted in step S103 together with the confirmation information from the electrode unit 20 to the control unit 3. Further, as shown in FIG. 18, step S210 is added to the flow chart in FIG. 7, and on the basis of the use information received from the electrode unit 20, whether or not the use state of the electrode unit 20 is appropriate is determined on the control unit 3 side. The determination method as to whether or not the use state of the electrode unit 20 is appropriate is similar to those in steps S104, S105 in FIG. 6.

In Embodiment 1 above, the start screen 300 in FIG. 8 and FIG. 9 is displayed at the control unit 3. However, in a case where induction of swallowing is controlled by a mobile phone of the patient, the start screen 300 may be displayed at the mobile phone of the patient.

In Embodiment 1 above, the start day and time and the end day and time in FIG. 4A are obtained by the clock function provided to the controller 121 of the electrode unit 20. However, at the times of start and end of operation, information of a time stamp may be transmitted from the control unit 3 side to the electrode unit 20, and on the basis of this information, the start day and time and the end day and time in FIG. 4A may be obtained.

In Embodiment 1 above, the process in FIG. 6 is performed by the controller 121 of the electrode unit 20. However, this process may be performed by the controller 111 of the holder unit 10. In this case, when the power supply button 11 has been turned on in step S101, the controller 111 performs communication with the controller 121 of the electrode unit 20, and obtains confirmation information and use information from the storage 23. Then, in step S102, the controller 121 waits for an information transmission request to be transmitted from the control unit 3. Then, upon receiving the information transmission request, the controller 121 performs processes of steps S103 to S107 on the basis of the confirmation information and the use information obtained from the electrode unit 20. In this case as well, the controller 121 may perform only transmission of the confirmation information and the use information without performing determination based on the use information as to whether or not the use state is appropriate, and determination as to whether or not use state is appropriate may be performed on the control unit 3 side.

In Embodiment 3 above, swallowing is detected through detection of displacement of the larynx part performed by the displacement sensor 61. However, swallowing may be detected through detection of a swallowing sound performed by a microphone. In this case, for example, a microphone is set in the inside or at the obverse surface of the holder unit 10 and the microphone only needs to be connected to the circuit board 130 inside the holder unit 10. In a case where a microphone is used in this manner, the displacement detection unit 60 may be omitted. In a case where a microphone is used, if a sound not less than a swallowing detection threshold has been detected by the microphone in a period in which apnea of the patient has been detected by a detection signal from the respiration detection unit 40, it may be determined that swallowing has occurred. In a case where both of the displacement detection unit 60 and a microphone are provided, if swallowing has been detected in both, it may be determined that swallowing has occurred in the patient.

Further, the electrode units 20 may be combined with the configuration of Embodiment 3 above, to allow a swallowing induction operation. Further, the present invention may be applied to a swallowing medical device other than the swallowing induction device 1 and the swallowing diagnosis device 7.

In Embodiments 1 to 3 above, the use information is managed in each electrode unit 20, the respiration detection unit 40, and the displacement detection unit 60. However, in a case where the control unit 3 to which the electrode unit 20, the respiration detection unit 40, and the displacement detection unit 60 are combined is uniquely determined, the use information may be managed in the control unit 3. In this case, for example, the control unit 3 may receive the serial number from each of the electrode unit 20, the respiration detection unit 40, and the displacement detection unit 60, and manage the use information of each unit in association with the received serial number. Similarly, in a case where the holder unit 10 to which the electrode unit 20 and the displacement detection unit 60 are combined is uniquely determined, the use information may be managed in the holder unit 10.

The use information of the electrode unit 20, the respiration detection unit 40, and the displacement detection unit 60 may be managed in a centralized manner by the server 220. For example, at the times of start of use and end of use of each device, the server 220 may receive the serial number from each of the electrode unit 20, the respiration detection unit 40, and the displacement detection unit 60 via the control unit 3, and may manage the use information of each unit in association with the received serial number.

The items of the use information and the confirmation information are not limited to those shown in FIGS. 4A, 4B. Some of these items may be deleted, or another item may be added to these items. For example, the encryption key may be omitted from the confirmation information, and a manufacturer code or the like may be added, instead of the encryption key.

In addition to the above, various modifications can be made as appropriate to the embodiments of the present invention, without departing from the scope of the technical idea defined by the claims.

What is claimed is:

1. A swallowing medical device configured to execute a medical operation regarding swallowing, the swallowing medical device comprising:
   an electrode configured to be attached to a target portion of a human body for the medical operation;
   control circuitry configured to control the medical operation; and
   a memory configured to store use information regarding a use state over time of the electrode, wherein
   the control circuitry executes a control for restricting use of the electrode on the basis of a fact that the use information does not satisfy a set condition for ensuring a characteristic of the electrode,
   the memory further stores confirmation information for confirming that the electrode is a genuine article, and
   the control circuitry executes the control for restricting use of the electrode on the basis of a fact that the electrode being a genuine article has not been able to be confirmed by the confirmation information.

2. The swallowing medical device according to claim 1, wherein
   the electrode is replaceable, and
   the memory is disposed at the electrode.

3. The swallowing medical device according to claim 2, wherein
   the control circuitry determines whether or not the use information satisfies the set condition.

4. The swallowing medical device according to claim 1, wherein
   the medical operation is a swallowing induction operation for inducing swallowing in a patient.

5. The swallowing medical device according to claim 4, wherein
   the electrode is configured to be attached to a pharynx part in order to provide stimulation for promoting swallowing, and
   the electrode is provided with
      an adhesive member being electrically conductive and being configured to cause the electrode to come into close contact with the target portion.

6. The swallowing medical device according to claim 4, further comprising:
   a respiration detection unit configured to be attached to a torso in order to detect respiration, and
   the respiration detection unit includes a stretch sensor configured to detect expansion and contraction, of the torso, that are associated with respiration.

7. The swallowing medical device according to claim 1, wherein
   the medical operation is a swallowing monitoring operation for monitoring swallowing in a patient.

8. The swallowing medical device according to claim 7, further comprising:
   a displacement detection unit configured to be attached to a larynx part in order to detect displacement of the larynx part, and
   the displacement detection unit includes a displacement sensor configured to detect displacement of the larynx part.

9. The swallowing medical device according to claim 8, wherein
   the control circuitry determines presence or absence of a risk of aspiration on the basis of a detection result by the electrode.

10. The swallowing medical device according to claim 7, further comprising:
    a respiration detection unit configured to be attached to a torso in order to detect respiration, and
    the respiration detection unit includes a stretch sensor configured to detect expansion and contraction, of the torso, that are associated with respiration.

11. The swallowing medical device according to claim 1, wherein
    the control circuitry stops the medical operation on the basis of a fact that the use information does not satisfy the set condition.

12. The swallowing medical device according to claim 1, comprising
    a display part configured to display information, wherein the control circuitry causes the display part to display report information for inhibiting use of the electrode, on the basis of a fact that the use information does not satisfy the set condition.

13. The swallowing medical device according to claim 12, wherein the control circuitry causes the display part to display information indicating a relationship between the use information and the set condition.

14. A non-transitory computer readable medium including executable instructions, which when executed by a computer cause the computer to execute a method for a swallowing medical device, the swallowing medical device executing a medical operation regarding swallowing and the swallowing medical device including an electrode configured to be attached to a target portion of a human body for the medical operation, the method comprising:

controlling the medical operation;

storing, in a memory of the swallowing medical device, use information regarding a use state over time of the electrode;

executing a control for restricting use of the electrode on the basis of a fact that the use information does not satisfy a set condition for ensuring a characteristic of the electrode; and storing, in the memory, confirmation information for confirming that the electrode is a genuine article, wherein the executing is an execution of the control for restricting use of the electrode on the basis of a fact that the electrode being a genuine article has not been able to be confirmed by the confirmation information.

\* \* \* \* \*